(12) United States Patent
Henry et al.

(10) Patent No.: US 10,167,498 B1
(45) Date of Patent: Jan. 1, 2019

(54) GRADIENT ELUTION MOVING BOUNDARY ELECTROPHORESIS FOR USE WITH COMPLEX SAMPLES AND DETECTION OF TOXINS

(71) Applicant: Applied Research Associates, Inc., Albuquerque, NM (US)

(72) Inventors: Alyssa Catharyn Henry, Arlington, VA (US); David Judson Ross, Silver Spring, MD (US)

(*) Notice: Subject to any disclaimer, the term of this patent is extended or adjusted under 35 U.S.C. 154(b) by 199 days.

(21) Appl. No.: 14/988,373

(22) Filed: Jan. 5, 2016

Related U.S. Application Data

(62) Division of application No. 12/761,515, filed on Apr. 16, 2010, now Pat. No. 9,261,482.

(51) Int. Cl.
*C12Q 1/46* (2006.01)
*C12Q 1/527* (2006.01)
(Continued)

(52) U.S. Cl.
CPC ............ *C12Q 1/46* (2013.01); *B01L 3/50273* (2013.01); *B01L 3/502715* (2013.01);
(Continued)

(58) Field of Classification Search
CPC ....... C12G 1/34; C12G 1/46; B01L 3/502715; B01L 3/502723; B01L 3/50273;
(Continued)

(56) References Cited

U.S. PATENT DOCUMENTS 5,098,826 A 3/1992 Wilkins et al.
5,482,608 A 1/1996 Keely et al.
(Continued)

OTHER PUBLICATIONS

D. Ross and J.G. Kralj, Simple Device for Multiplexed Electrophoretic Separations Using Gradient Elution Moving Boundary Electrophoresis with Channel Current Detection, Anal. Chem., vol. 80, pp. 9467-9474 (2008).*
(Continued)

*Primary Examiner* — Maris R Kessel
(74) *Attorney, Agent, or Firm* — Dinsmore & Shohl LLP; Monika Jaensson; Hallie O'Brien

(57) ABSTRACT

Methods of detecting the presence of toxins in a sample using electrophoretic separations and of performing electrophoretic separation of complex samples are provided. The method of detecting the presence of toxins includes reacting a sample and a substrate with a signaling enzyme which converts the substrate to the product in a reaction medium, introducing a run buffer into a separation channel having an inlet end, selectively introducing at least one of the substrate and the product of the reaction medium into the inlet end of the separation channel, electrophoretically separating the substrate and the product, and determining the rate of conversion of the substrate to the product, wherein a change in the rate of conversion is indicative of the presence of toxins. The method of performing electrophoretic separations of complex samples having charged particulates and oppositely charged analytes comprising introducing a run buffer into a separation channel having an inlet end, selectively introducing the oppositely charged analytes in the complex sample into the separation channel, and electrophoretically separating the charged particulates and the oppositely charged analytes. Additionally, a device for varying with respect to time the bulk flow of a fluid in a separation channel of an electrophoretic device having a buffer reservoir in fluid contact with the separation channel is provided. The device includes a pressure sensor in fluid contact with a buffer reservoir, a high pressure reservoir in selective fluidic communication with the buffer reservoir, a low pressure reservoir in selective fluidic communication with the buffer reservoir and in fluidic communication with the high pressure reservoir, and a pumping device for
(Continued)

pumping a gas from the low pressure reservoir to the high pressure reservoir.

12 Claims, 18 Drawing Sheets

(51) Int. Cl.
*B01L 3/00* (2006.01)
*G01N 27/447* (2006.01)

(52) U.S. Cl.
CPC ... *B01L 3/502723* (2013.01); *B01L 3/502738* (2013.01); *B01L 3/502753* (2013.01); *C12Q 1/527* (2013.01); *G01N 27/4476* (2013.01); *G01N 27/44704* (2013.01); *G01N 27/44791* (2013.01); *B01L 2300/14* (2013.01); *B01L 2400/0421* (2013.01); *B01L 2400/0605* (2013.01); *B01L 2400/082* (2013.01); *G01N 2333/918* (2013.01); *G01N 2333/988* (2013.01); *G01N 2550/00* (2013.01)

(58) Field of Classification Search
CPC ........... B01L 3/502753; B01L 2300/14; B01L 2400/0421; B01L 2400/0605; B01L 2400/082; G01N 27/44704; G01N 27/4476; G01N 27/44791; G01N 2333/918; G01N 2333/988; G01N 2550/00

See application file for complete search history.

(56) References Cited

U.S. PATENT DOCUMENTS

| | | | |
|---|---|---|---|
| 5,958,202 | A | 9/1999 | Regnier et al. |
| 6,110,696 | A | 8/2000 | Brown et al. |
| 7,029,561 | B2 | 4/2006 | Ross et al. |
| 7,537,680 | B2 | 5/2009 | Ross et al. |
| 7,572,357 | B2 | 8/2009 | Ross et al. |
| 8,080,144 | B2 | 12/2011 | Ross et al. |
| 2004/0206626 | A1 | 10/2004 | Ross et al. |

OTHER PUBLICATIONS

J. Wang, et al., Microchip enzymatic assay of organophosphate nerve agents, Analytica Chimica Act, vol. 505, pp. 183-187 (2004).*
A. G. Hadd, et al., Microfluidic Assays of Acetylcholinesterase Inhibitors, Anal. Chem., vol. 71, pp. 5206-5212 (1999).*
J. M. Ford, et al., Serum concentrations of tacrine hydrochloride predict its adverse effects in Alzheimer's disease, Clinical Pharmacology & Therepeutics, vol. 53, No. 6, pp. 691-695 (Jun. 1993).*
Shackman et al., Electrophoretic Separations in Small Spaces: Gradient Elution Moving-Boundary Electrophoresis (GEMBE), The 10th International Conference on Miniaturized Systems for Chemistry and Life Sciences, Nov. 5-9, 2006, pp. 912-914, Tokyo, Japan.
Tiselius, A New Apparatus for Electrophoretic Analysis of Colloidal Mixtures, Trans Faraday Soc, vol. 33, pp. 524-531, Jan. 25, 1937.
Savitzky et al., Smoothing and Differentiation of Data by Simplified Least Squares Procedures, Anal Chem, vol. 36, pp. 1627-1639 (1964).
Dittrich, et al., Micro Total Analysis Systems. Latest Advancements and Trends, Anal Chem, vol. 78, pp. 3887-3907 (2006).
E.X. Vrouwe, et al., Direct Measurement of Lithium in Whole Blood Using Microchip Capillary Electrophoresis With Integrated Conductivity Detection, Electrophoresis vol. 25, pp. 1660-1667 (2004).
Strawbridge, et al., Measurement of Particle Size Distributions in Milk Homogenized by a Microfiuidizer: Estimation of Populations of Particles with Radii Less Than 100nm, Journal of Colloid and Interface Science, vol. 171, Issue 2, May 1995, pp. 392-398.
Suarez-Luque, et al., Determination of Major Metal Cations in Milke by Capillary Zone Electrophoresis, International Dairy Journal, vol. 17, Issue 8, pp. 896-901, Aug. 2007.
Shackman, et al., Gradient Elution Moving Boundary Electrophoresis for High-Throughput Multiplexed Microfluidic Devices, Anal. Chem. 28, pp. 565-571, 2007.
Strychalski, et al., Microfluidic Analysis of Complex Samples with Minimal Sample Preparation Using Gradient Elution Moving Boundary Electrophoresis, Anal. Chem., vol. 81, No. 24, pp. 10201-10207, 2009.
Luttge, et al., Microchip Analysis of Lithium in Blood Using Moving Boundary Electrophoresis and Zone Electrophoresis, Electrophoresis, vol. 26, pp. 3032-3042, 2005.
Heiger, et al., Determination of Small Ions by Capillary Zone Electrophoresis with Indirect Photometric Detection, Environmental and Food Analysis, Application Note, Agilent Technologies, 1994.
Breadmore, et al., Determination of Ribavirin in Human Serum and Plasma by Capillary Electrophoresis, Electrophoresis, vol. 25, pp. 1615-1622, 2004.
Forsyth, Ford, Truman, Roberts, Wilcock; Determination of tacrine hydrochloride in human serum by chloroform extraction, reversed-phase high-performance liquid chromatography and fluorimetric detection; Journal of Chromatography, 1988, 433, 352-358; Netherlands.

* cited by examiner

GRADIENT ELUTION MOVING BOUNDARY ELECTROPHORESIS FOR USE WITH COMPLEX SAMPLES AND DETECTION OF TOXINS

CROSS-REFERENCE TO RELATED APPLICATIONS

The present application is filed under 35 U.S.C. § 111 as a divisional of U.S. application Ser. No. 12/761,515, filed on Apr. 16, 2010, the contents of which are hereby incorporated by reference in their entirety.

STATEMENT OF GOVERNMENT RIGHTS

This invention was made with government support under the National Institute of Standards and Technology (NIST)/Applied Research Associates Cooperative Research and Development Agreement (CRADA) No. CN-10-0001. The United States government may have certain rights in this invention.

TECHNICAL FIELD

The present invention relates generally to methods of detecting toxins using electrophoretic separations, and relates particularly to methods of detecting toxins using enzymatic assays coupled with gradient elution moving boundary electrophoresis. The present invention also relates to methods of performing electrophoretic separations of complex samples, and relates particularly to methods of performing electrophoretic separations of complex samples using gradient elution moving boundary electrophoresis. Additionally, the present invention also relates to a device for varying with respect to time the bulk flow of a fluid, and relates particularly to a device for varying with respect to time the variable bulk flow of a fluid in a separation channel of an electrophoretic device.

BACKGROUND

Chemical warfare involves the use of toxins as weapons to kill, injure, or incapacitate. Toxins are poisonous substances produced by living cells, organisms, and/or artificial processes. Some examples of toxins include nerve agents and pesticides. Many nerve agents and pesticides are organophosphates, which function by irreversibly inhibiting acetylcholinesterase.

Acetylcholinesterase is a serine esterase that is anchored to the surface of the post-synaptic membrane. Acetylcholinesterase hydrolytically degrades acetylcholine to yield acetate and choline. Inhibition of acetylcholinesterase results in an increase in the concentration of acetylcholine, a neurotransmitter responsible for the influx of $Ca^{2+}$ ions and an action potential that triggers muscle contraction. Thus, when acetylcholinesterase is inhibited, acetylcholine triggers repeated influxes of $Ca^{2+}$ ions and repeated muscle contractions, resulting in paralysis and eventual death by suffocation. Thus, the detection of toxins is of wide import. Moreover, the ability to detect toxins in the field is necessary.

Many detection mechanisms are known in the art. Several examples of detection mechanisms include ion mobility spectrometry, differential mobility spectrometry, Raman spectroscopy, and capillary electrophoresis. These detection mechanisms are limited, however, in that they require the use of devices which, while technically portable, are heavy and bulky. Moreover, capillary electrophoresis is limited with regard to toxins as toxins must typically be detected at lower concentrations than is permitted by conductivity detection. As a result, additional embodiments for the detection of toxins are needed.

Moreover, the ability to detect toxins in complex samples, such as soil, is desirable. Typically, the separation and purification of complex samples using traditional separation techniques is tedious. In the field of capillary electrophoresis, complex samples containing particulates must be filtered before they may be analyzed to prevent particulates from entering the separation capillary. When particulates enter the separation capillary, the accuracy of detection is compromised due to a variety of factors, including: a noisy detector signal, interruption of electrophoretic current, clogging of the separation capillary, and fouling of the inner surface of the separation capillary resulting in irreproducible measurements. Thus, additional embodiments for detecting toxins in complex samples are needed.

Recently, gradient elution moving boundary electrophoresis ("GEMBE") has been developed. GEMBE is an electrophoretic separation technique which combines electrophoresis and pressure-based separation techniques. More particularly, GEMBE involves applying an electric potential to a sample and controlling the variable bulk flow of the sample, to obtain sequential separation of sample components. GEMBE is advantageous over other electrophoretic separation techniques in that it does not require sample injection, does not employ moving parts, provides electrophoretic separations over short separation lengths, and provides high data quality.

We have discovered that GEMBE may be employed to indirectly detect the presence of toxins in a sample by reacting the sample with an enzyme in a reaction medium containing a substrate for the enzyme. Additionally, we have discovered that GEMBE may be employed to perform electrophoretic separations of complex samples with little or no sample preparation. Finally, we have developed a novel, field portable device for varying with respect to time the bulk flow of a fluid, which may be employed in GEMBE.

SUMMARY

In one embodiment, a method of indirectly detecting the presence of toxins in a sample using electrophoretic separations is provided, the method comprising reacting the sample with a signaling enzyme in a reaction medium containing a substrate for the signaling enzyme, wherein the signaling enzyme converts the substrate to a product, introducing a run buffer into a separation channel having an inlet end, selectively introducing at least one of the substrate and the product of the reaction medium into the inlet end of the separation channel, electrophoretically separating the substrate and the product by applying an electric potential (i.e. field strength) across the separation channel and varying with respect to time the bulk flow of the run buffer in the separation channel, wherein the substrate and the product are sequentially detected and quantified, and determining the rate of conversion of the substrate to the product, wherein a change in the rate of conversion is indicative of the presence of toxins.

In another embodiment, a method of performing electrophoretic separations of complex samples having charged particulates and oppositely charged analytes is provided, the method comprising introducing a run buffer into a separation channel having an inlet end, selectively introducing the oppositely charged analytes in the complex sample into the inlet end of the separation channel, and electrophoretically separating the charged particulates and the oppositely charged analytes by applying an electric potential across the separation channel and varying with respect to time the bulk flow of the run buffer in a direction substantially aligned with the electric potential, wherein the oppositely charged analytes are sequentially detected and quantified.

In yet another embodiment, a device for varying with respect to time the flow of a fluid in a separation channel of an electrophoretic device having a buffer reservoir in fluid contact with the separation channel is provided. The device comprises a pressure sensor, a high pressure reservoir, a low pressure reservoir, and pumping device for pumping a gas from the low pressure reservoir to the high pressure reservoir. The pressure sensor is in fluid contact with the buffer reservoir, wherein the pressure sensor detects the pressure of the fluid. The high pressure reservoir is in selective fluidic communication with the buffer reservoir and in fluidic communication with the high pressure reservoir. The device comprises a first operating condition a second operating condition, and a third operating condition, in which the high pressure reservoir is in fluid communication with the buffer reservoir in the first operating condition, such that the buffer reservoir reaches a threshold pressure, the buffer reservoir is in fluid communication with the low pressure reservoir in the second operating condition, such that a pressure ramp over time is initiated such that the pressure is varied from a starting pressure value to an ending pressure value, and the high pressure reservoir is in fluid communication with the buffer reservoir in the third operating condition, such that the buffer reservoir reaches a final pressure level, wherein the variable bulk flow of the fluid is varied.

In another embodiment, a method of varying with respect to time the bulk flow of a fluid in a separation channel of an electrophoretic device which comprises utilizing the device for varying with respect to time the bulk flow of a fluid in a separation channel of electrophoretic device having a buffer reservoir in fluid contact with the separation channel according to the present invention is provided.

These and other features and advantages of these and other various embodiments according to the present invention will become more apparent in view of the drawings, detailed description, and claims provided herein.

BRIEF DESCRIPTION OF THE DRAWINGS

The following detailed description of the embodiments of the present invention can be better understood when read in conjunction with the following drawings, where like structure is indicated with like reference numerals, and in which.

Figure 1:
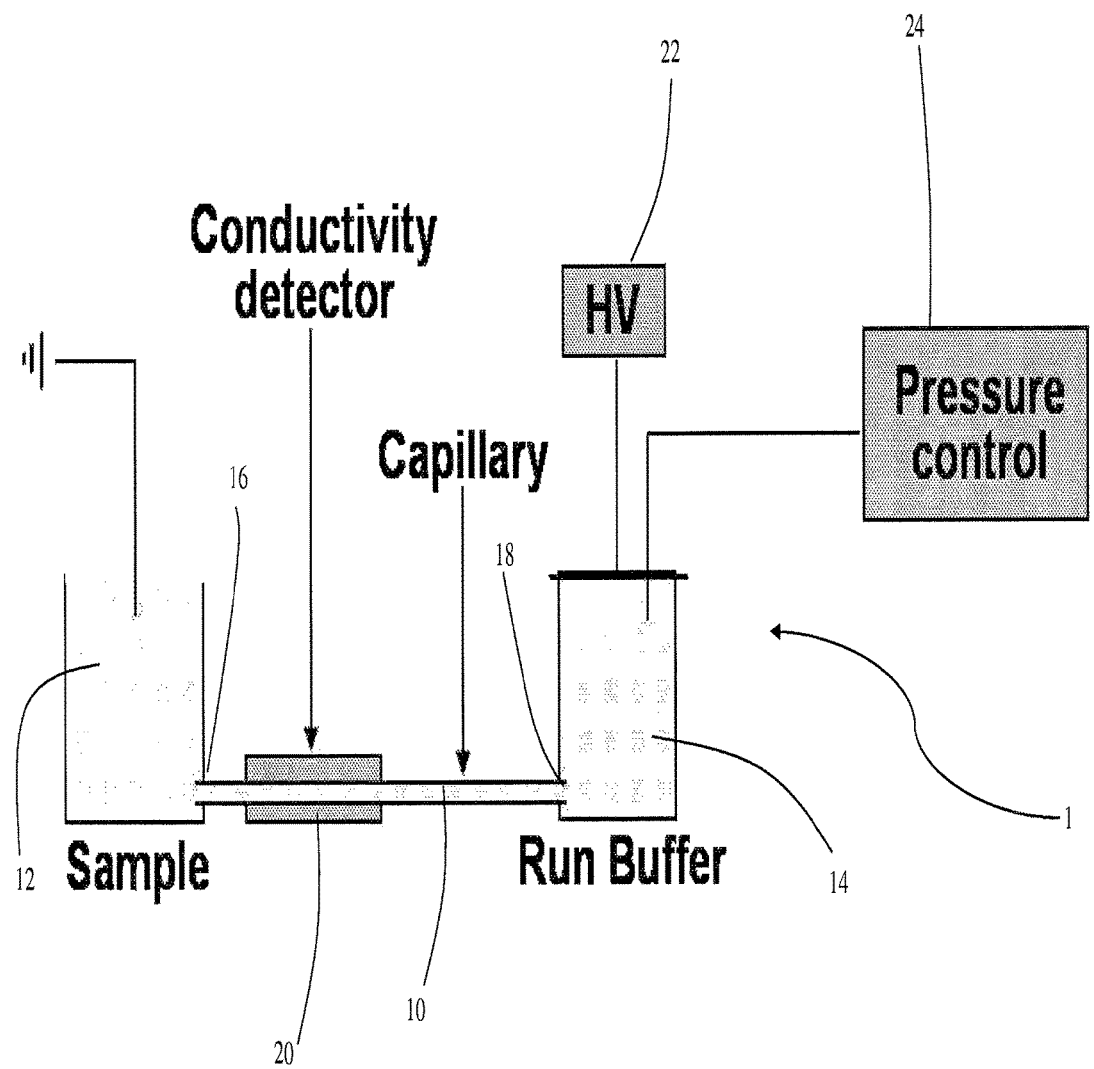
FIG. 1 is a schematic of a gradient elution moving boundary electrophoresis ("GEMBE") device which can be used in accordance with embodiments of the present invention.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present invention.

DETAILED DESCRIPTION

The following terms are used in the present application:

As used herein, the term "toxin" refers to a poisonous substance produced by living cells, organisms, and/or artificial processes.

As used herein, the term "sample" refers to a substance and/or mixture of substances, and combinations thereof, to be analyzed with electrophoretic separations. In one aspect, the "sample" comprises toxins such that the presence and/or concentration of toxins may be detected.

As used herein, the term "electrophoretic separations" refers to the migration of charged molecules through a solution under the influence of an applied electric potential. In one aspect, the term "electrophoretic separations" refers to electrophoretic separations performed using gradient elution moving boundary electrophoresis.

As used herein, the term "signaling enzyme" refers to a biological molecule that is capable of catalyzing a chemical reaction. In one aspect, the "signaling enzyme" is sensitive to the presence of a toxin. In the context of a signaling enzyme, the term "sensitive to the presence of a toxin" refers to a signaling enzyme having biological activity which is affected by the presence of a toxin. In one aspect, "sensitive to the presence of a toxin" refers to a signaling enzyme having biological activity which is affected and/or changed by the presence of a toxin, wherein the toxin stimulates the activity of the signaling enzyme or inhibits the activity of the signaling enzyme.

As used herein, the term "activity" refers to a quantitative determination of the rate of enzymatic conversion of a substrate to a product.

As used herein, the term "substrate" refers to a molecule upon which a signaling enzyme can act. As used herein, the term "product" refers to a molecule that is formed by the signaling enzyme acting upon the substrate.

As used herein, the term "reaction medium" refers to a fluid comprising an electrophoretic buffer and/or a reaction buffer, and combinations thereof. In one particular aspect, the "reaction medium" comprises a reaction buffer, an enzyme, a substrate, and/or a sample, and combinations thereof.

As used herein, the term "run buffer" refers to a fluid comprising an electrophoretic buffer.

As used herein, the term "separation channel" refers to a channel wherein electrophoretic separation of the substrate, product, charged particulates, and/or charged analytes, and combinations thereof, occurs under the influence of an applied electric potential.

As used herein, the term "electric potential" refers to the electrostatic potential energy divided by the charge in a circuit expressed in volts. In the context of electrophoretic separations, the "electric potential" is imposed across and substantially along the length of the separation channel.

As used herein, the terms "variable bulk flow" and "bulk flow" are used interchangeably to refer to the combination of electroosmotic flow and controlled, variable pressure-driven flow that is varied over time during an electrophoretic separation. As used herein, the term "changing the bulk flow velocity" refers to altering the rate of a variable bulk flow, such that sequential separation of substrates, products, charged particulates and/or charged analytes, and combinations thereof, may be achieved.

As used herein, the term "sequentially detected and quantified" refers to the consecutive detection of the substrate, the product, the charged particulates, and/or the oppositely charged analytes, and combinations thereof, following differential migration of the substrate, the product, the charged particulates, and/or the oppositely charged analytes, and combinations thereof, through the separation channel.

As used herein, the terms "detect", "detection", and/or "detecting" are used interchangeably to refer to determining the presence and/or concentration of toxins and/or analytes, and combinations thereof.

In the context of determining the rate of conversion of the substrate to the product, the term "change in the rate of conversion" refers to an increase or a decrease in the activity of signaling enzyme.

As used herein, the term "control sample assay" refers to an enzymatic assay wherein a signaling enzyme is reacted with a substrate in a reaction medium, wherein the signaling enzyme converts the substrate to a product, and wherein the substrate and the product are detected by GEMBE in the absence of a toxin.

As used herein, the term "nerve agent" refers to a class of organophosphates that disrupt the mechanism by which nerves transfer messages by blocking acetylcholinesterase. As used herein, the term "pesticide" refers to a class of nerve agents that are used to kill pests. As used herein, the term "endotoxin" refers to a toxic molecules derived from bacteria which are released when the bacteria are lysed. As used herein, the terms "organophosphate" and "organophosphates" are used interchangeably to refer to phosphorous-containing organic molecules.

As used herein, the term "complex sample" refers to a substance containing charged particulates and/or oppositely charged analytes, and combinations thereof.

As used herein, the term "charged particulates" refers to particles of solid and/or liquid suspended in a gas or liquid possessing an electric charge. As used herein, the term "oppositely charged analytes" refers to molecules possessing an electric charge that is of an opposite sign of the charged particulate and/or charged particulates.

As used herein the terms "stimulant", "stimulate", "stimulated", and "stimulation" are used interchangeably to refer to the ability of a toxin to increase the activity of a signaling enzyme. As used herein, the terms "inhibitor", "inhibit", "inhibited", and "inhibition" are used interchangeably to refer to the ability of a toxin to decrease the activity of a signaling enzyme.

As used herein, the terms "fluidic" and "fluid" are used interchangeably to refer to a liquid and/or a gas, and combinations thereof.

As used herein, the terms "varying the bulk flow" and/or "controlling the variable bulk flow" are used interchangeably to refer to regulating the rate of a bulk flow, such that sequential separation of analytes may be achieved.

As used herein, the term "buffer reservoir" refers to a reservoir which contains a fluid.

As used herein, the term "pressure sensor" refers to a device for monitoring the pressure of the fluid in the buffer reservoir. More particularly, the term "pressure sensor" refers to a device for monitoring the pressure of a gas in the headspace of the buffer reservoir.

As used herein, the term "high pressure reservoir" refers to a reservoir which contains a fluid, wherein the reservoir has a higher than ambient pressure when the pumping device pumps a gas from the low pressure reservoir to the high pressure reservoir.

As used herein, the term "low pressure reservoir" refers to a reservoir which contains a fluid, wherein the reservoir has a lower than ambient pressure when the pumping device pumps a gas from the low pressure reservoir to the high pressure reservoir.

As used herein, the terms "selective fluid communication" and "selective fluidic communication" are used interchangeably to refer to the transfer of a fluid from one position to another position, wherein the fluid communication can be opened, closed, and/or set in between an open and a closed position, and combinations thereof.

As used herein, the terms "fluid communication" and "fluidic communication" are used interchangeably to refer to the transfer of a fluid from one position to another position. In one particular aspect, the terms "fluid communication" and "fluidic communication" are used interchangeably to refer to the unidirectional transfer of a fluid from one position to another position.

As used herein, the term "threshold pressure level" refers to an initial positive value of pressure in the buffer reservoir that is preferred for sample loading and/or other manipulations. In one aspect, electrophoretic separation can be initiated after the pressure in the buffer reservoir reaches the "threshold pressure level."

As used herein, the term "pressure ramp" refers to varying the pressure in the buffer reservoir, such that sequential separation of analytes may be achieved.

As used herein, the term "starting pressure value" refers to the pressure in the buffer reservoir at the beginning of the pressure ramp.

As used herein, the term "ending pressure value" refers to the pressure in the buffer reservoir at the end of the pressure ramp.

As used herein, the term "final pressure level" refers to a positive ending value of pressure in the buffer reservoir. In one aspect, electrophoretic separation can be concluded after the pressure in the buffer reservoir reaches the "final pressure level."

As used herein, the term "selective venting communication" refers to the transfer of a fluid from one position to the ambient environment, wherein the fluid communication can be opened, closed, and/or set in between an open and a closed position, and combinations thereof.

As used herein, the terms "vary the pressure of the fluid" and "control the variable bulk flow" are used interchangeably to refer to increasing and/or decreasing the pressure of a fluid.

As used herein, the term "resist pressure variation of a fluid" refers to decreasing the rate at which the pressure of a fluid is varied.

Embodiments of the present invention relate to methods of indirectly detecting the presence of toxins, methods of performing electrophoretic separations of complex samples, and a device for varying with respect to time the bulk flow of a fluid in a separation channel of an electrophoretic device. In one embodiment, a method of indirectly detecting the presence of toxins in a sample using electrophoretic separations is provided. In one aspect of this embodiment, the method comprises reacting the sample with a signaling enzyme in a reaction medium containing a substrate for the signaling enzyme, wherein the signaling enzyme converts the substrate to a product, introducing a run buffer into a separation channel having an inlet end, selectively introducing at least one of the substrate and the product of the reaction medium into the inlet end of the separation channel, electrophoretically separating the substrate and the product by applying an electric potential across the separation channel and varying with respect to time the bulk flow of the run buffer in the separation channel, wherein the substrate and the product are sequentially detected and quantified, and determining the rate of conversion of the substrate to the product, wherein a change in the rate of conversion is indicative of the presence of toxins.

In one aspect, the method of indirectly detecting the presence of toxins in a sample using electrophoretic separations comprises reacting a sample with a signaling enzyme in a reaction medium containing a substrate for the signaling enzyme, wherein the signaling enzyme converts the substrate to a product. In one aspect, the signaling enzyme is a biological catalyst that is sensitive to the presence of a toxin. In one particular aspect, the signaling enzyme is selected from the group consisting of oxidoreductases, transferases, hydrolases, lyases, isomerases, and/or ligases, and combinations thereof. In a further aspect, the signaling enzyme is an esterase. In still a further aspect, the signaling enzyme is acetylcholinesterase. Acetylcholinesterase is a serine esterase which hydrolytically degrades acetylcholine to yield acetate and choline, as shown in equation (I) below:

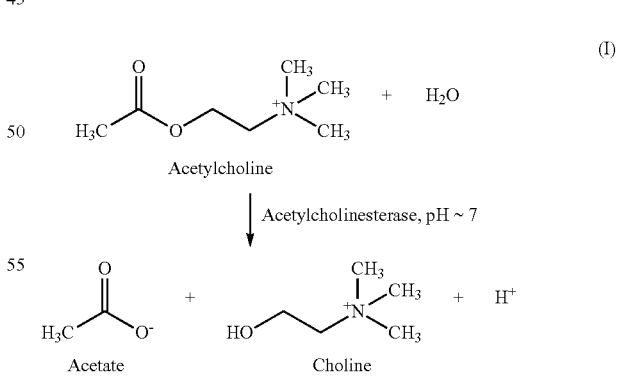

In another aspect, the signaling enzyme is a cyclase. In a further aspect, the signaling enzyme is adenylate cyclase. Adenylate cyclase is a lyase which converts adenosine triphosphate ("ATP") to cyclic adenosine monophosphate ("cAMP") and pyrophosphate, as shown in equation (II) below:

(II)

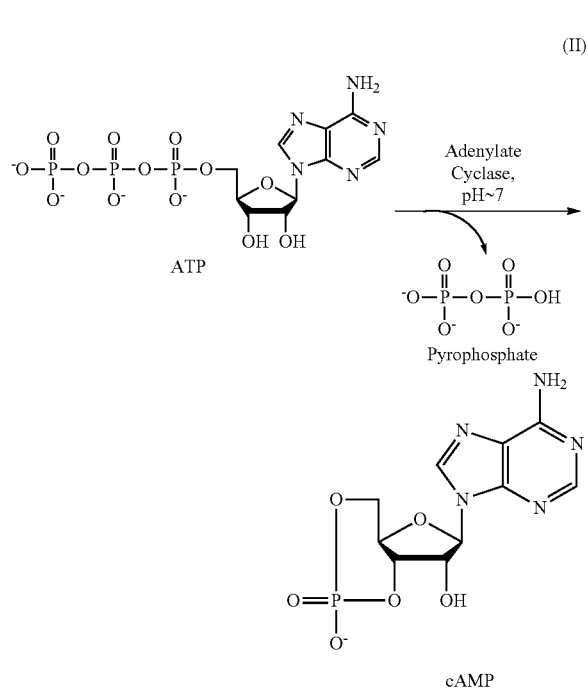

In one aspect, the substrate for the signaling enzyme is a molecule upon which the signaling enzyme can act. In one particular aspect, the signaling enzyme acts upon the substrate by converting the substrate to a product. In a further aspect wherein the signaling enzyme is acetylcholinesterase, the substrate is acetylcholine and the products are acetate and choline. In this particular aspect, acetylcholinesterase acts upon acetylcholine by converting acetylcholine to acetate and choline. In another aspect wherein the signaling enzyme is adenylate cyclase, the substrate is ATP and the products are pryophosphate and cAMP. In this particular aspect, adenylate cyclase acts upon ATP by converting ATP to pyrophosphate and cAMP.

In another aspect, a sample is reacted with a signaling enzyme in a reaction medium containing a substrate for the signaling enzyme, wherein the signaling enzyme converts the substrate to a product. Initiation of the chemical reaction depends upon the mixing of the sample, signaling enzyme, and substrate in the reaction medium. In one particular aspect, the sample comprises at least one toxin. In a further aspect, the sample comprises at least one toxin that is an inhibitor of the signaling enzyme and/or an enhancer of a signaling enzyme. In still a further aspect, the sample comprises at least one toxin that is a nerve agent.

In one particular aspect wherein the signaling enzyme is acetylcholinesterase, the sample comprises at least one acetylcholinesterase inhibitor. Acetylcholinesterase is irreversibly inhibited by alkylphosphofluoridates and/or related organophosphates. Alkylphosphofluoridates and organophosphates irreversibly inhibit acetylcholinesterase by interacting with a serine residue ("Ser") in the active site of acetylcholinesterase. One example of an alkylphosphofluoridate is diisopropylphosphofluoridate ("DIPF"). In a further aspect, acetylcholinesterase is inhibited by organophosphates. In yet a further aspect, acetylcholinesterase is inhibited by organophosphates which are nerve agents. In yet still a further aspect, the acetylcholinesterase is inhibited by nerve agents which are pesticides. Examples of suitable acetylcholinesterase inhibitors that are nerve agents include tabun, sarin, soman, cyclosarin, tacrine, VE, VG, VM, VR, VX, and/or Novichok agents, and combinations thereof. Examples of suitable acetylcholinesterase inhibitors that are pesticides include dichlorvos, malathion, parathion, and/or malaoxon, and combinations thereof.

In an alternative aspect wherein the signaling enzyme is adenylate cyclase, the sample comprises at least one adenylate cyclase stimulant. In a further aspect, the adenylate cyclase stimulant is an endotoxin. In still a further aspect, the endotoxin is derived from the bacteria, *Salmonella*.

In a further aspect, the signaling enzyme is sensitive to the presence of a toxin. In one aspect, the signaling enzyme is sensitive to the presence of a toxin such that the toxin affects the activity of the signaling enzyme. In a further aspect, the toxin affects the activity of the signaling enzyme by stimulating the activity of the signaling enzyme and/or by inhibiting the activity of the signaling enzyme. In one particular aspect wherein the signaling enzyme is adenylate cyclase, a toxin which stimulates the activity of adenylate cyclase results in a decrease in the concentration of ATP and an increase in the concentration of pyrophosphate and cAMP. Thus, the presence of a toxin capable of stimulating adenylate cyclase can be indirectly detected by monitoring the concentrations of ATP and cAMP. In an alternative aspect wherein the signaling enzyme is acetylcholinesterase, a toxin which inhibits the activity of acetylcholinesterase results in an increase in the concentration of acetylcholine and a decrease in the concentration of choline. Thus, the presence of a toxin capable of inhibiting acetylcholinesterase can be indirectly detected by monitoring the concentrations of acetylcholine and choline.

In another aspect, the sample is reacted with a signaling enzyme in a reaction medium. In one particular aspect, the reaction medium is a solution comprising a suitable reaction buffer. In a further aspect, the reaction buffer provides reaction conditions wherein the signaling enzyme retains its activity. The reaction medium and/or the reaction buffer should comprise a pH wherein the signaling enzyme maintains its biological activity, such that the signaling enzyme can act upon the substrate. Additionally, the reaction should be performed at a temperature wherein the signaling enzyme maintains its biological activity, such that the signaling enzyme can act upon the substrate.

In a further aspect, the reaction medium comprises a suitable electrophoretic buffer. In one particular aspect, a suitable electrophoretic buffer comprises a conductive aqueous buffered ionic solution. In a further aspect, the electrophoretic buffer has a pKa at or near the desired working pH. In still a further aspect, the electrophoretic buffer has a concentration of approximately 100 mmol/L.

In another aspect of this embodiment, the method of indirectly detecting the presence of toxins in a sample using electrophoretic separations comprises introducing a run buffer into a separation channel having an inlet end. In this particular aspect, the run buffer is contained within the run buffer reservoir.

In another aspect, the method of indirectly detecting the presence of toxins in a sample using electrophoretic separations comprises selectively introducing at least one of the substrate and the product of the reaction medium into the inlet end of the separation channel. In one particular aspect, the substrate and the product of the reaction medium are introduced into the inlet end of the separation channel by electrokinetic pumping. In another aspect, the separation channel comprises a capillary tube or a microfluidic channel. In a further aspect, the separation channel is a capillary tube having a cross-sectional area of less than about 0.1 mm². In still a further aspect, the capillary tube has a cross-sectional area from about 100 μm² to about 20,000 μm².

As shown in FIG. 1, in one particular aspect, the separation channel 10 is a capillary tube comprising a substantially straight channel with a sample reservoir 12 at the inlet end 16 of the separation channel 10 and a run buffer reservoir 14 at the outlet end 18 of the separation channel 10. In a further aspect, a conductivity detector 20 in fluid contact with the separation channel 10 detects the presence and/or concentration of the substrate and/or the product.

In yet another aspect of this embodiment, the method of indirectly detecting the presence of toxins in a sample using electrophoretic separations comprises electrophoretically separating the substrate and the product. The substrate and the product are electrophoretically separated by applying an electric potential across the separation channel 10 and varying with respect to time the bulk flow of the run buffer in the separation channel, wherein the substrate and the product are sequentially detected and quantified. In one particular aspect, the substrate and the product are electrophoretically separated using gradient elution moving boundary electrophoresis ("GEMBE"), as described in U.S. patent application Ser. No. 11/866,589.

Referring again to FIG. 1, in one aspect, the substrate and the product are electrophoretically separated by applying an electric potential across the separation channel 10. In one particular aspect, the electric potential is applied by a voltage control device 22. In a further aspect, the voltage control device comprises an anode and a cathode (not shown). The voltage control device 22 is electrically connected to the inlet end 16 and the outlet end 18 of the separation channel 10. In this particular aspect, the electric potential is applied across and substantially along the length of the separation channel 10 between the sample reservoir 12 and the run buffer reservoir 14. In one particular aspect, the cathode of the voltage control device 22 is electrically connected to the inlet end 16 of the separation channel 10 and the anode is electrically connected to the outlet end 18 of the separation channel 10. In an alternative aspect, the cathode of the voltage control device 22 is electrically connected to the outlet end 18 of the separation channel 10 and the anode is electrically connected to the inlet end 16 of the separation channel 10. In this way, the voltage control device 22 can be configured to control the direction of the flow of the charged molecules during an electrophoretic separation.

In one aspect, a suitable electric potential to be applied to the separation channel 10 can be determined through the application of Ohm's Law Plots for a given separation column and background electrolyte. In one particular aspect, the field strength applied along the length of the separation channel is from about 20 V/cm to about 10,000 V/cm. In a further aspect, the field strength applied along the length of the separation channel is from about 20 V/cm to about 2000 V/cm. In still a further aspect, the field strength applied along the length of the channel is about 400 V/cm.

In yet another aspect, the substrate and the product are electrophoretically separated by varying with respect to time the bulk flow of the run buffer in the separation channel. Variable bulk flow is a combination of electroosmotic flow ("EOF") and controlled, variable pressure-driven flow that is increased and/or decreased, and combinations thereof, gradually over an electrophoretic separation. EOF arises when a surface charge is present along the separation channel 10, such that oppositely charged ions in the reaction medium are drawn towards the charged separation channel 10 forming an electrical double layer which can be mobilized axially when an electric potential is applied along the length of the separation channel 10. The mobile oppositely charged ions cause EOF of the reaction medium through viscous drag.

In one particular aspect, the separation channel 10 comprises a glass-based material wherein the surface silanol groups exhibit net negative charges at a pH of above approximately 2. Thus, positively charged ions in the reaction medium are drawn towards the negatively charged surface forming an electrical double layer. In a further aspect wherein the signaling enzyme is acetylcholinesterase, the substrate is acetylcholine, and the products are acetate and choline, the positively charged acetylcholine and choline are drawn towards the negatively charged surface of the separation channel 10, forming an electrical double layer.

As previously discussed, the electrical double layer can be mobilized axially when an electric potential is applied across and substantially along the length of the separation channel 10, creating EOF. In one aspect, the direction of the EOF is dependent upon the connectivity of the anode and the cathode and also upon the surface charge present along the separation channel 10.

In one particular aspect, the surface of the separation channel 10 can be coated with a dynamic coating to reverse the charge present along the separation channel 10. In this way, the direction of the EOF can be reversed. In one particular aspect, the EOF can be in the same direction as the controlled, variable pressure-driven flow; in another aspect, the EOF can be in a direction opposite to that of the controlled, variable pressure-driven flow. For example, where the separation channel 10 is positively charged, a negatively charged dynamic coating can be applied to the separation channel 10. Similarly, where the separation channel 10 is negatively charged, a positively charged dynamic coating can be applied to the separation channel 10. In one particular aspect, the positively charged dynamic coating is didodecyldimethyl-ammonium bromide ("DDAB").

As shown in FIG. 1, in one particular aspect, the variable bulk flow is controlled by a regulated pressure control device 24. The regulated pressure control device 24 is configured to create a variable pressure-driven flow. In one aspect, the variable pressure-driven flow is in substantially the same direction as the EOF. In an alternative aspect, the variable pressure-driven flow is in substantially the opposite direction as the EOF. In one aspect, the pressure differential varies with time throughout the electrophoretic separation such that the substrate and the product are sequentially detected and quantified. In one particular aspect, the regulated pressure control device 24 creates a pressure differential of from about −60,000 Pa to about 60,000 Pa. In a further aspect, the regulated pressure control device 24 creates a pressure differential of from about −30,000 Pa to about 30,000 Pa. In still a further aspect, the regulated pressure control device 24 creates a pressure differential of about 10,000 Pa.

By modifying the bulk flow, for example, by inducing a flow counter to the EOF, the resolution of an electrophoretic separation can be increased. In a further aspect, sequential separation of the substrate and the product is achieved by changing the bulk flow velocity over time such that the substrate and the product in the reaction medium are sequentially introduced into the separation channel 10 and are sequentially separated within the separation channel 10.

Where high resolution is sought, the direction of the bulk flow of the reaction medium and the electrophoretic migration of the substrate and the product in the reaction medium should be in opposite directions. Where the direction of the bulk flow is opposite to that of the electrophoretic migration of the substrate and the product in the reaction medium, only molecules with electrophoretic velocities that are greater than the bulk fluid velocity are introduced into the separation channel 10. In one aspect, at the beginning of the electrophoretic separation, the bulk flow should be set such that substantially all of the substrate and the product in the reaction medium are precluded from being introduced the separation channel 10. However, the bulk flow is variable such that it can be changed over time to allow introduction of the substrate and the product in the reaction medium into the separation channel 10.

Still referring to FIG. 1, the regulated pressure control device 24 is connected to either the sample reservoir 12 or the run buffer reservoir 14. In one particular aspect, the regulated pressure control device 24 is connected to the run buffer reservoir 14. The regulated pressure control device 24 operates by creating a pressure differential across the inlet end 16 and the outlet end 18 of the separation channel 10.

Detection of the presence and/or concentration of the substrate and/or the product depends upon electrophoretic transport of the substrate and/or the product to a detector 20. In one aspect, the detection of the substrate and/or product is employed to indirectly determine the presence of a toxin. In one particular aspect, the detection of a decrease in the formation of a product, or the detection of an increase in substrate are an indirect indication of the presence of a toxin. In a further aspect, wherein the signaling enzyme is acetylcholinesterase, wherein the substrate is acetylcholine, and wherein the products are acetate and choline, acetylcholine and choline are detected to indirectly determine the presence of a toxin. More particularly, in one aspect, a decrease in the concentration of acetylcholine is indicative of the presence of toxins. In an alternative aspect, the detection of an increase in the formation of a product, or the detection of a decrease in substrate are an indirect indication of the presence of a toxin. In a further aspect, wherein the signaling enzyme is adenylate cyclase, wherein the substrate is ATP, and wherein the products are pyrophosphate and cAMP, pyrophosphate and/or cAMP are detected to indirectly determine the presence of a toxin. In this particular aspect, an increase in the concentration of pyrophosphate and/or cAMP is indicative of the presence of toxins.

Where determination of the substrate and/or product is quantitative, the conversion of the substrate to the product or the depletion of the product will be stoichiometric. For stoichiometric conversion of the substrate to the product, measurement of the product detected can be used to calculate the amount of toxin present in the sample.

In one aspect, the substrate and the product are sequentially detected by a detector 20. In one particular aspect, the detector 20 is a detection electrode and/or a conductivity detector. As shown in FIG. 1, in a further aspect, the detector 20 is a conductivity detector. However, the detector 20 should not be limited to the detectors 20 disclosed herein, but may comprise any detector 20 that is usable with other electrophoretic techniques known in the art.

In another aspect, the substrate and the product are sequentially quantified. In this particular aspect, quantification of the substrate and the product is performed by determining the rate of conversion of substrate to the product from the concentration of the substrate and the product. In one particular aspect, the substrate and the product are sequentially detected and quantified at a single time point. In this particular aspect, the quantification is performed by determining the rate of conversion ("ROC") of the substrate to the product. In a further aspect, the rate of conversion of substrate to the product is determined by dividing the concentration of the product ("[P]") by the time between introducing the reaction medium into the inlet end 16 of the separation channel 10, ("T1"), and the time of detection, ("T2"), as set forth in equation (III).

$$ROC = \frac{[P]}{T2 - T1} \quad \text{(III)}$$

In an alternative aspect, the substrate and the product are sequentially detected and quantified at a plurality of time points. In this particular aspect, detection of the substrate and the product is repeated periodically to measure the rate of change of the product concentration.

In a further aspect, the rate of conversion of the substrate to the product is compared with the rate of conversion of the substrate to product in a control sample assay to determine the presence of toxins. An increase or a decrease in rate of conversion is indicative of the presence of a toxin. In one particular aspect, the concentration of the substrate and the product are quantified at a series of four time points, corresponding to ~2 minutes, ~5 minutes, ~7.5 minutes, and ~10.5 minutes.

In another aspect, the sample is a complex sample. In a further aspect, the complex sample is selected from the group consisting of soil, mud, dirt, milk, apple juice, estuarine sediment, coal fly ash, blood serum, tomato leaves, peach leaves, citrus leaves, and/or calf serum. In this particular aspect, the complex sample comprises negatively charged particulates.

In another embodiment, a method of performing electrophoretic separations of complex samples having charged particulates and oppositely charged analytes is provided. The method comprises introducing a run buffer into a separation channel having an inlet end, selectively introducing the oppositely charged analytes in the complex sample into the inlet end of the separation channel, and electrophoretically separating the charged particulates and the oppositely charged analytes by applying an electric potential across the separation channel and varying with respect to time the bulk flow of the run buffer in a direction substantially aligned with the electric potential, wherein the oppositely charged analytes are sequentially detected and quantified.

In one aspect, the method comprises introducing a run buffer into a separation channel having an inlet end. In this particular aspect, the run buffer is contained within the run buffer reservoir. In another aspect, the method comprises selectively introducing the oppositely charged analytes in the complex sample into the inlet end of the separation channel. In one particular aspect, the complex sample is soil, mud, dirt, milk, apple juice, estuarine sediment, coal fly ash, blood serum, tomato leaves, peach leaves, citrus leaves, and/or calf serum, and combinations thereof. In a further aspect, the charged particulates are negatively charged. In a further aspect, the oppositely charged analytes are positively charged. In one particular aspect, the oppositely charged analytes comprise potassium, calcium, sodium, magnesium, lithium, and/or melamine, and combinations thereof. However, the oppositely charged analytes should not be limited to those described herein, but may comprise any analyte possessing an electric charge opposite that of the charged particulates.

In another aspect, the reaction medium is a solution comprising a suitable reaction buffer. In a further aspect, the reaction buffer provides reaction conditions wherein the signaling enzyme retains its activity. The reaction medium and/or the reaction buffer should comprise a pH wherein the signaling enzyme maintains its biological activity, such that the signaling enzyme can act upon the substrate. Additionally, the reaction should be performed at a temperature wherein the signaling enzyme maintains its biological activity, such that the signaling enzyme can act upon the substrate.

In a further aspect, the reaction medium comprises a suitable electrophoretic buffer. In one particular aspect, a suitable electrophoretic buffer comprises a conductive aqueous buffered ionic solution. In a further aspect, the electrophoretic buffer has a pKa at or near the desired working pH. In still a further aspect, the electrophoretic buffer has a concentration of less than about 200 mmol/L to avoid excessive conductivity.

The method of performing electrophoretic separations of complex samples comprises selectively introducing the oppositely charged analytes in the complex sample into the inlet end of the separation channel. In one particular aspect, the oppositely charged analytes is introduced into the inlet end of the separation channel by electrokinetic pumping. In another aspect, the separation channel comprises a capillary tube or a microfluidic channel. In a further aspect, the separation channel is a capillary tube having a cross-sectional area of less than about 0.1 mm$^2$. In still a further aspect, the capillary tube has a cross-sectional area from about 10 μm$^2$ to about 20,000 μm$^2$.

In another aspect, the separation channel is a capillary tube or a microfluidic channel. In a further aspect, as shown in FIG. 1, the separation channel 10 is a capillary tube and comprises a substantially straight channel with a sample reservoir 12 at the inlet end 16 of the separation channel 10 and a run buffer reservoir 14 at the outlet end 18 of the separation channel 10. In still a further aspect, a conductivity detector 20 is in fluid contact with the separation channel 10 such that the conductivity detector 20 detects the presence and/or concentration of charged particulates and/or the oppositely charged analytes.

In yet another aspect of this embodiment, the method of performing electrophoretic separations of complex samples comprises electrophoretically separating the charged particulates and the oppositely charged analytes. In one particular aspect, the charged particulates and the oppositely charged analytes are electrophoretically separated by applying an electric potential across the separation channel and varying with respect to time the bulk flow of the run buffer in a direction substantially aligned with the electric potential, wherein the oppositely charged analytes are sequentially detected and quantified. In one particular aspect, the charged particulates and the oppositely charged analytes are electrophoretically separated using GEMBE, as described in U.S. patent application Ser. No. 11/866,589.

Referring again to FIG. 1, in one aspect, the charged particulates and the oppositely charged analytes are electrophoretically separated by applying an electric potential across the separation channel 10. In one particular aspect, the electric potential is applied by a voltage control device 22. In a further aspect, the voltage control device 22 comprises an anode and a cathode (not shown). In this particular aspect, the electric potential is applied substantially along the length of the separation channel 10 between the sample reservoir 12 and the run buffer reservoir 14. In one particular aspect, the voltage control device 22 is electrically connected to the inlet end 16 and the outlet end 18 of the separation channel 10. In a further aspect, the cathode of the voltage control device 22 is electrically connected to the inlet end 16 of the separation channel 10 and the anode is electrically connected to the outlet end 18 of the separation channel 10. In an alternative aspect, the cathode of the voltage control device 22 is electrically connected to the outlet end 18 of the separation channel 10 and the anode is electrically connected to the inlet end 16 of the separation channel 10. In this way, the voltage control device 22 can be configured to control the direction of the flow of the charged molecules during an electrophoretic separation.

In one aspect, the electric potential applied to the separation channel can be determined through the application of Ohm's Law Plots for a given separation column and background electrolyte. In one particular aspect, the field strength applied along the length of the separation channel is from about 20 V/cm to about 10,000 V/cm. In a further aspect, the field strength applied along the length of the separation channel is from about 20 V/cm to about 2,000 V/cm. In still a further aspect, the field strength applied along the length of the channel is about 400 V/cm.

In yet another aspect, the charged particulates and the oppositely charged analytes are electrophoretically separated by varying with respect to time the bulk flow of the run buffer in a direction substantially aligned with the electric potential. As previously discussed, variable bulk flow is a combination of EOF and controlled, variable pressure-driven flow that is decreased gradually over an electrophoretic separation. In one aspect, the EOF is based upon the presence of a surface charge along the separation channel. In one particular aspect, the separation channel 10 comprises a glass-based material wherein the surface silanol groups exhibit net negative charges at a pH of above approximately 2. Thus, positively charged ions in the reaction medium are drawn towards the negatively charged surface forming an electrical double layer. In a further aspect wherein the charged particulate is negatively charged and the oppositely charged analytes are positively charged, the positively charged analytes are drawn towards the negatively charged surface of the separation channel 10, forming an electrical double layer.

In one particular aspect, the surface of the separation channel 10 can be coated with a dynamic coating to reverse the charge present along the separation channel 10. In this way, the direction of the EOF can be reversed. In one particular aspect, the EOF can be in the same direction as the controlled, variable pressure-driven flow; in another aspect, the EOF can be in a direction opposite to that of the controlled, variable pressure-driven flow. For example, where the separation channel 10 is positively charged, a negatively charged dynamic coating can be applied to the separation channel 10. Similarly, where the separation channel 10 is negatively charged, a positively charged dynamic coating can be applied to the separation channel 10. In one particular aspect, the positively charged dynamic coating is didodecyldimethyl-ammonium bromide ("DDAB").

Referring to FIG. 1, in one particular aspect, the variable bulk flow is controlled by a regulated pressure control device 24. The regulated pressure control device 24 is configured to create a variable pressure-driven flow. In one particular aspect, the regulated pressure control device creates a pressure differential across the inlet end 16 and outlet end 18 of the separation channel 10. In a further aspect, the variable pressure-driven flow is in substantially the same direction as the EOF. In an alternative aspect, the variable pressure driven flow is in substantially the opposite direction as the EOF. In one aspect, the pressure differential varies with time throughout the electrophoretic separation such that the substrate and the product are sequentially detected and quantified. In one particular aspect, the regulated pressure control device 24 creates a pressure differential of from about −60,000 Pa to about 60,000 Pa. In a further aspect, the regulated pressure control device 24 creates a pressure differential of from about −30,000 Pa to about 30,000 Pa. In still a further aspect, the regulated pressure control device 24 creates a pressure differential of about 10,000 Pa. In another aspect, the pressure differential varies with time at a rate from about −1 Pa/s to about −1000 Pa/s. In a further aspect, the pressure differential varies with time at a rate from about −10 Pa/s to about −500 Pa/s. In still a further aspect, the pressure differential varies with time at a rate of about −300 Pa/s.

In a further aspect, sequential separation of the oppositely charged analytes is achieved by changing the bulk flow velocity over time such that the oppositely charged analytes in the reaction medium are sequentially introduced into the separation channel 10 and are sequentially separated within the separation channel 10.

Where high resolution is sought, the direction of the bulk flow of the reaction medium and the electrophoretic migration of the oppositely charged analytes in the reaction medium should be in opposite directions. Where the direction of the bulk flow is opposite to that of the EOF of the oppositely charged analytes in the reaction medium, only molecules with electrophoretic velocities that are greater than the bulk fluid velocity are introduced into the separation channel 10. In one aspect, at the beginning of the electrophoretic separation, the bulk flow should be set such that substantially all of the oppositely charged analytes in the reaction medium are precluded from being introduced the separation channel 10. However, the bulk flow is variable such that it can be changed over time to allow introduction of the oppositely charged analytes in the reaction medium into the separation channel 10.

Still referring to FIG. 1, the regulated pressure control device 24 is connected to either the sample reservoir 12 or the run buffer reservoir 14. In one particular aspect, the regulated pressure control device 24 is connected to the run buffer reservoir 14. The regulated pressure control device 24 operates by creating a pressure differential across the inlet end 16 and the outlet end 18 of the separation channel 10.

In another aspect, the method of performing electrophoretic separations of complex samples comprises electrophoretically separating the charged particulates and the oppositely charged analytes, wherein the oppositely charged analytes are sequentially detected and quantified. Detection of the presence and/or concentration of the oppositely charged analytes depends upon electrophoretic transport of the oppositely charged analytes to a detector 20. In one particular aspect, the detector 20 is a detection electrode and/or a conductivity detector. As shown in FIG. 1, in a further aspect, the detector 20 is a conductivity detector. However, the detector 20 should not be limited to the detectors 20 disclosed herein, but may comprise any detector 20 that is usable with other electrophoretic techniques known in the art.

In a further aspect, sequential separation of the oppositely charged analytes is achieved by changing the bulk flow velocity over time such that the oppositely charged analytes are sequentially separated from the reaction medium into the separation channel.

In another embodiment, a device for varying with respect to time the bulk flow of a fluid in a separation channel of an electrophoretic device having a buffer reservoir in fluid contact with the separation channel is provided. The device comprises a pressure sensor, a high pressure reservoir, a low pressure reservoir, and pumping device for pumping a gas from the low pressure reservoir to the high pressure reservoir. The pressure sensor is in fluid contact with the buffer reservoir, wherein the pressure sensor detects the pressure of the fluid. The high pressure reservoir is in selective fluidic communication with the buffer reservoir and in fluidic communication with the high pressure reservoir. The device comprises a first operating condition, a second operating condition, and a third operating condition, in which the high pressure reservoir is in fluid communication with the buffer reservoir in the first operating condition, such that the buffer reservoir reaches a threshold pressure level, the buffer reservoir is in fluid communication with the low pressure reservoir in the second operating condition, such that a pressure ramp over time is initiated such that the pressure is varied from a starting pressure value to an ending pressure value, and the high pressure reservoir is in fluid communication with the buffer reservoir in the third operating condition, such that the buffer reservoir reaches a final pressure level, wherein the variable bulk flow of the fluid is varied.

Figure 12:
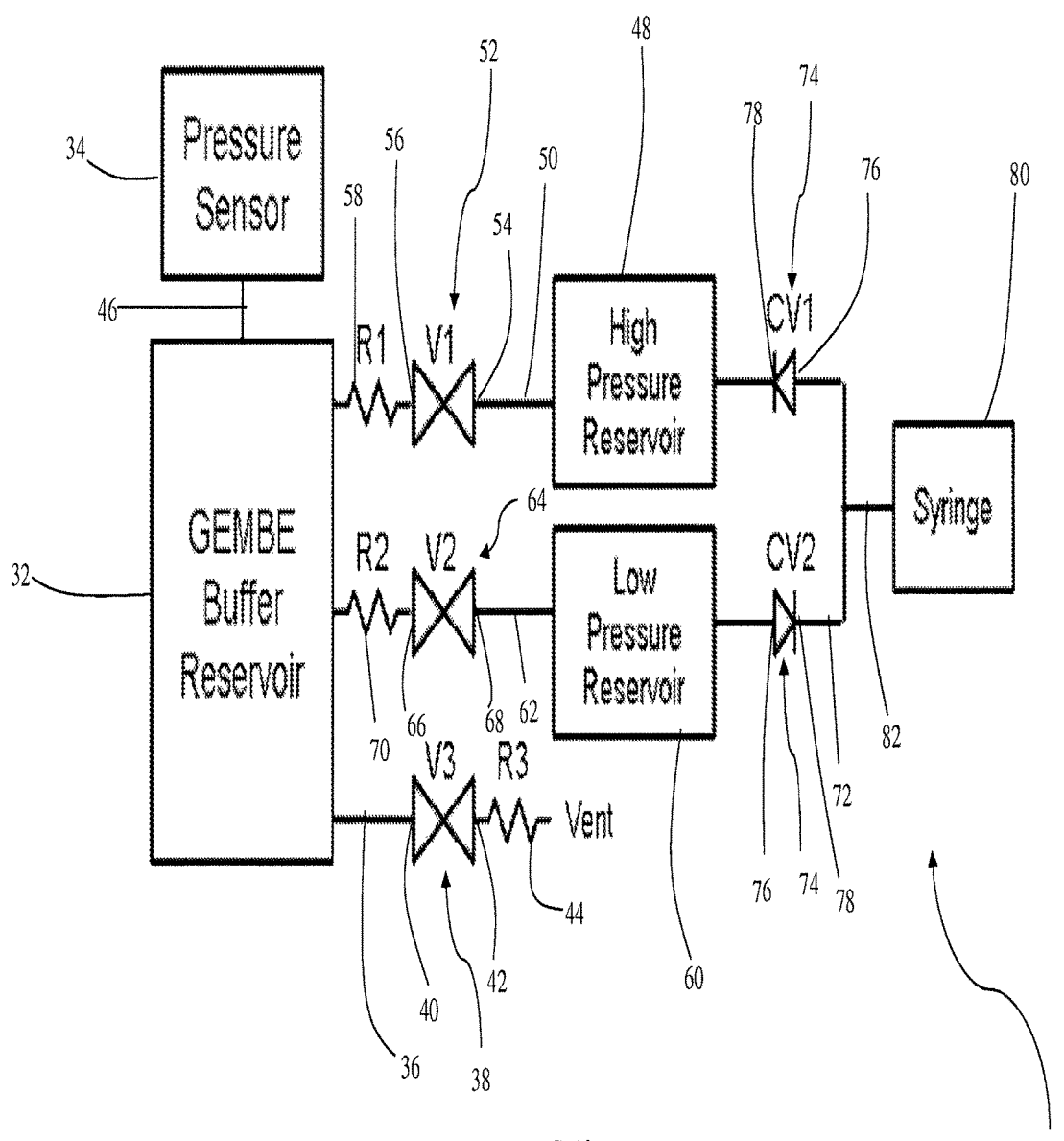
FIG. 12 is a schematic of a device for varying with respect to time the bulk flow of a fluid in a separation channel of an electrophoretic device according to an embodiment of the present invention.
Figure 13:
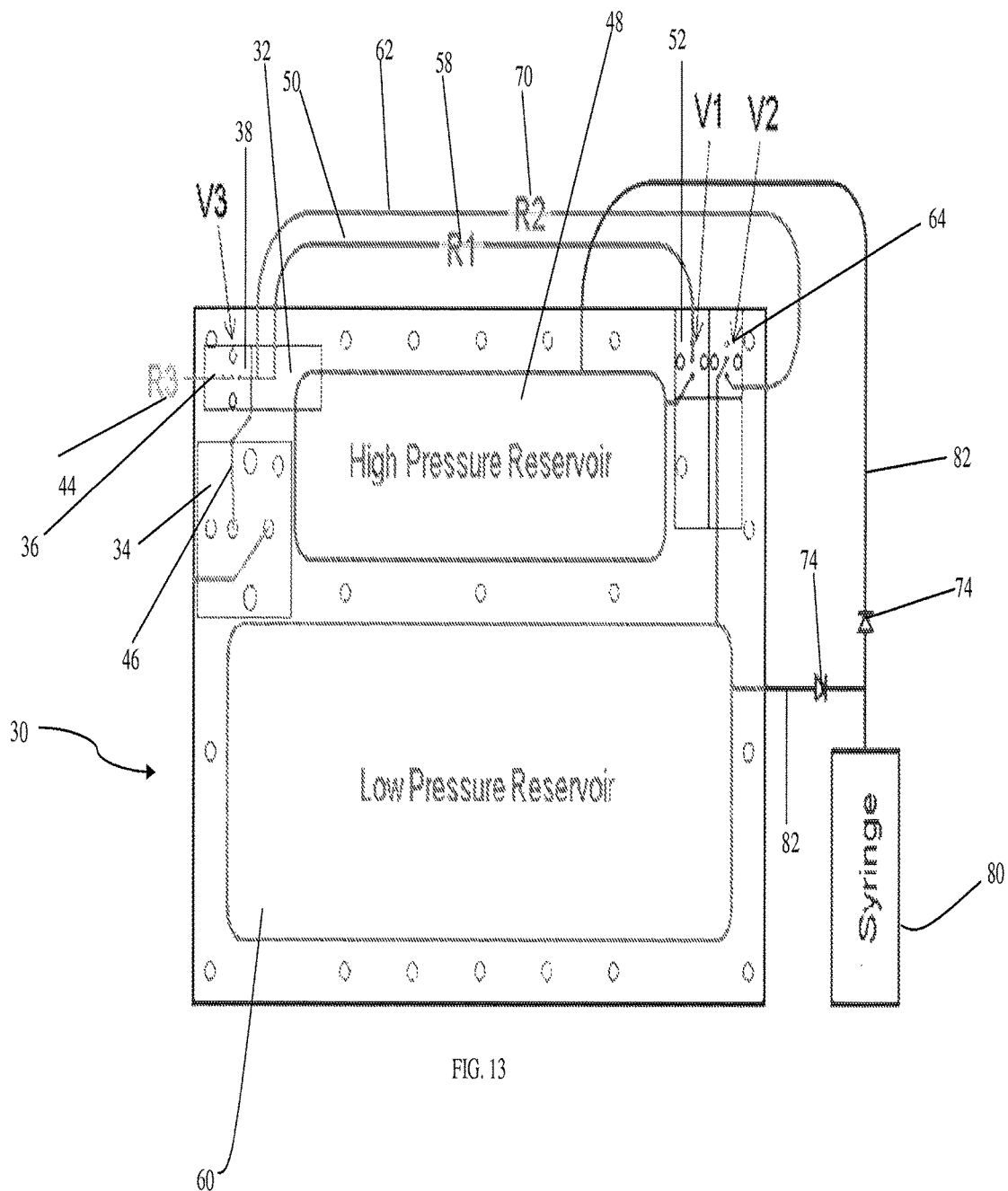
FIG. 13 is a schematic of a device for varying with respect to time the bulk flow of a fluid in a separation channel of an electrophoretic device according to an embodiment of the present invention.

As shown in FIGS. 1, 12, and 13, in one aspect, the device 30 for varying with respect to time the bulk flow of a fluid in a separation channel 10 of an electrophoretic device 1 having a buffer reservoir 32 in fluid contact with the separation channel 10 comprises a pressure sensor 34 in fluid contact with the buffer reservoir 32. In one particular aspect, the electrophoretic device is a GEMBE device 1, as described in U.S. patent application Ser. No. 11/866,589. In a further aspect wherein the electrophoretic device is a GEMBE device 1, the buffer reservoir 32 comprises a sample reservoir 12 or a run buffer reservoir 14. In still a further aspect, the buffer reservoir 32 is a run buffer reservoir 14. In one particular aspect, the buffer reservoir 32 is sealed to the ambient atmosphere, such that the pressure can be set to a value different from the pressure of the ambient atmosphere.

In another aspect, the buffer reservoir 32 contains a fluid (not shown). In a further aspect, the buffer reservoir 32 contains a fluid which is an electrophoretic buffer. In still a further aspect, the buffer reservoir 32 comprises a total volume of approximately ~4 mL, and contains ~2 mL of electrophoretic buffer.

In a further aspect, the buffer reservoir 32 is in selective venting communication with the ambient atmosphere. In one particular aspect, the buffer reservoir 32 is in selective venting communication with the ambient atmosphere with a tube and/or conduit 36. In still a further aspect, the tube and/or conduit 36 is in fluid communication with a valve 38, which operates to vary the pressure of the fluid.

In a further aspect, the valve 38 is a control valve. The control valve 38 comprises an inlet end 40 and an outlet end 42. The control valve 38 has an open position and a closed position. In the open position, fluid is able to flow through the control valve 38, such that the buffer reservoir 32 is vented to the ambient atmosphere. More particularly, in the open position, fluid enters the control valve 38 through the inlet end 40 and exits the control valve 38 through the outlet end 42. In the closed position, fluid is unable to flow through the control valve 38. More particularly, in the closed position, fluid is unable to exit the control valve 38 through the outlet end 42. In one aspect, the control valve 38 includes but should not be limited to ball valves, gate valves, and/or plug valves. In one particular aspect, the control valve 38 is a solenoid valve. In still a further aspect, the solenoid valve is controlled through a miniature data acquisition device.

In a further aspect, the valve 38 is fluidly connected to a flow resistor 44. In one particular aspect, the valve 38 is fluidly connected to the flow resistor 44 such that when in the open position, fluid enters the valve 38 through the inlet end 40, exits the valve 38 through the outlet end 42, and enters the flow resistor 44. Alternatively, when in the open position, fluid enters the flow resistor 44, enters the valve 38 through the inlet end 40, and exits the valve 38 through the outlet end 42. In another aspect, larger values of flow resistance for the flow resistor 44 will result in longer time for increasing the pressure in the device 30. In one particular aspect, the flow resistor 44 comprises tubing. In a further aspect, the tubing is polyetheretherketone ("PEEK") tubing. In yet a further aspect, the PEEK tubing comprises an inner diameter of about 0.001 inches to about 0.010 inches.

In another aspect, the pressure sensor 34 is in fluid contact with the buffer reservoir 32, wherein the pressure sensor 34 detects the pressure of the fluid. In one aspect, the pressure sensor 34 is in fluid contact with the buffer reservoir 32 with a tube and/or conduit 46. In a further aspect, the pressure sensor 34 is a solid-state pressure sensor. In still a further aspect, the pressure sensor 34 is monitored through a miniature data acquisition device.

As shown in FIGS. 12 and 13, in yet another aspect, the device 30 for varying with respect to time the bulk flow of a fluid comprises a high pressure reservoir 48 in selective fluidic communication with the buffer reservoir 32. In one particular aspect, the high pressure reservoir 48 is in selective fluidic communication with the buffer reservoir 32 with a tube and/or conduit 50. In a further aspect, the tube and/or conduit 50 is in fluid communication with a valve 52, which operates to vary the pressure of the fluid.

In a further aspect, the valve 52 is a control valve. The control valve 52 comprises an inlet end 54 and an outlet end 56. The control valve 52 has an open position and a closed position. In the open position, fluid is able to flow through the control valve 52, such that the high pressure reservoir 48 is in fluid communication with the buffer reservoir 32. More particularly, in the open position, fluid enters the control valve 52 through the inlet end 54 and exits the control valve 52 through the outlet end 56. In the closed position, fluid is unable to flow through the control valve 52. More particularly, in the closed position, fluid is unable to exit the control valve through the outlet end 56. In one aspect, the control valve 52 includes but should not be limited to ball valves, gate valves, and plug valves. In one particular aspect, the control valve is a solenoid valve. In still a further aspect, the solenoid valve is controlled through a miniature data acquisition device.

In a further aspect, the valve 52 is fluidly connected to a flow resistor 58. In one particular aspect, the valve 52 is fluidly connected to the flow resistor 58 such that when in the open position, fluid enters the valve 52 through the inlet end 54, exits the valve 52 through the outlet end 56, and enters the flow resistor 58. Alternatively, when in the open position, fluid enters the flow resistor 58, enters the valve 52 through the inlet end 54, and exits the valve 52 through the outlet end 56. In one aspect, the flow resistor 58 is chosen so that the pressure in the buffer reservoir 32 will rise at a rate such that it can be monitored with the pressure sensor 34. Larger values of flow resistance for the flow resistor 58 will result in longer time for increasing the pressure in the device 30. In one particular aspect, the flow resistor 58 comprises tubing. In a further aspect, the tubing is PEEK tubing. In yet a further aspect, the PEEK tubing comprises an inner diameter of about 0.001 inches to about 0.010 inches.

Still referring to FIGS. 12 and 13, in another aspect, the low pressure reservoir 60 is in selective fluidic communication with the buffer reservoir 32 and is also in fluidic communication with the high pressure reservoir 48. In one particular aspect, the low pressure reservoir 60 is in selective fluidic communication with the buffer reservoir 32 with a tube and/or conduit 62. In a further aspect, the tube and/or conduit 62 is in fluid communication with a valve 64, which operates to vary the pressure of the fluid.

In a further aspect, the valve 64 is a control valve. The control valve 64 comprises an inlet end 66 and an outlet end 68. The control valve 64 has an open position and a closed position. In the open position, fluid is able to flow through the control valve 64, such that the buffer reservoir 32 is in fluid communication with the low pressure reservoir 60. More particularly, in the open position, fluid enters the control valve 64 through the inlet end 66 and exits the control valve 64 through the outlet end 68. In the closed position, fluid is unable to flow through the control valve 64. More particularly, in the closed position, fluid is unable to exit the control valve 64 through the outlet end 68. The control valve 64 has an open position and a closed position. In the open position, fluid is able to flow through the control valve 64. In the closed position, fluid is unable to flow through the control valve 64. In one aspect, the control valve 64 includes but should not be limited to ball valves, gate valves, and plug valves. In one particular aspect, the control valve 64 is a solenoid valve. In still a further aspect, the solenoid valve is controlled through a miniature data acquisition device.

In a further aspect, the valve 64 is fluidly connected to a flow resistor 70. In one particular aspect, the valve 64 is fluidly connected to the flow resistor 70 such that when in the open position, fluid enters the valve 64 through the inlet end 66, exits the valve 64 through the outlet end 68, and enters the flow resistor 70. Alternatively, when in the open position, fluid enters the flow resistor 70, enters the valve 64 through the inlet end 66, and exits the valve 64 through the outlet end 68. In one aspect, the flow resistor 70 is chosen to achieve a desired electrophoretic separation. For example, in one aspect, a lower value of the flow resistor 70 will result in a faster pressure ramp and a correspondingly faster electrophoretic separation with lower resolution. Conversely, a higher value of the flow resistor 70 will result in a slower pressure ramp and a slower electrophoretic separation with higher resolution. In one particular aspect, the flow resistor 70 comprises tubing. In a further aspect, the tubing is PEEK tubing. In yet a further aspect, the PEEK tubing comprises an inner diameter of about 0.001 in to about 0.010 in.

In one particular aspect, the low pressure reservoir 60 is also in fluidic communication with the high pressure reservoir 48. In one particular aspect, the low pressure reservoir 60 is in fluidic communication with the high pressure reservoir 48 with a tube and/or conduit 72. In a further aspect, the tube and/or conduit 72 is in fluid communication with at least one valve 74, which operates to vary the pressure of the fluid. In one particular aspect, the tube and/or conduit 72 is in fluid communication with a pair of check valves 74.

In this particular aspect, the valve 74 is a check valve. The check valve 74 comprises an inlet end 76 and an outlet end 78. The check valve 74 restricts the flow of the fluid to one direction. In one particular aspect, fluid is able to flow through the check valve 74, such that the low pressure reservoir 60 is in fluid communication with the high pressure reservoir 48. In this particular aspect, fluid enters the check valve 74 through the inlet end 76 and exits the check valve 74 through the outlet end 78. In a further aspect, fluid enters the check valve 74 from the low pressure reservoir 60 and exits the check valve 74 to the high pressure reservoir 48. In an alternative aspect, fluid enters the check valve 74 from the high pressure reservoir 48 and exits the check valve 74 to the low pressure reservoir 60. In one particular aspect, the check valve has a cracking pressure of ~1 psi.

Still referring to FIGS. 12 and 13, in another aspect, the device 30 for varying with respect to time the bulk flow of a fluid comprises a pumping device 80 for pumping a gas from the low pressure reservoir 60 to the high pressure reservoir 48. In one particular aspect, the pumping device 80 is disposed between the low pressure reservoir 60 and the high pressure reservoir 48. In a further aspect, the pumping device 80 is disposed between the pair of check valves 74. In another aspect, the pumping device 80 is in fluidic communication with the high pressure reservoir 48 with a tube and/or conduit 82. In one particular aspect, the pumping device 80 comprises a piston pump. In a further aspect, the piston pump is a syringe. In still a further aspect, the piston syringe is a 20 mL polypropylene syringe.

In one particular aspect, wherein the device 30 for varying with respect to time the bulk flow of a fluid is used with a GEMBE device 1, the pumping device 80 is pumped at least once to pump a gas from the low pressure reservoir 60 to the high pressure reservoir 48. In a further aspect wherein the pumping device 80 is pumped at least once, the valve 52 and the valve 64 are in a closed position, such that the fluid is unable to flow through the valves, 52, 64. In this particular aspect, a higher than ambient pressure in the high pressure reservoir 48 is created. In a further aspect, a lower than ambient pressure in the low pressure reservoir 60 is created.

In an alternative aspect, the device 30 for varying with respect to time the bulk flow of a fluid comprises a plurality of pumping devices 80. In this particular aspect, the plurality of pumping devices 80 are disposed between the low pressure reservoir 60 and the high pressure reservoir 48. In one particular aspect, one of the plurality of pumping devices 80 pumps a gas from the ambient atmosphere to the high pressure reservoir 48. In an alternative aspect, another of the plurality of pumping devices 80 pumps a gas from the low pressure reservoir 60 to the ambient atmosphere. In a further aspect, a plurality of check valves are employed to regulate the flow of the gas when the plurality of pumping devices 80 are pumping gases. In one particular aspect, four check valves are employed to regulate the flow of the gas when the plurality of pumping devices 80 are pumping gases.

In one particular aspect, the device 30 for varying with respect to time the bulk flow of a fluid in a separation channel 10 has a first operating condition, a second operating condition, and a third operating condition. In the first operating condition, the high pressure reservoir 48 is in fluid communication with the buffer reservoir 32, such that the buffer reservoir 32 reaches a threshold pressure level. The pressure in the buffer reservoir 32 is monitored with the pressure sensor 34. In one particular aspect, the threshold pressure level is a positive value. In a further aspect, the threshold pressure level is from about 1,000 Pa to about 100,000 Pa. In still a further aspect, the threshold pressure level is from about 5,000 Pa to about 50,000 Pa. In yet still a further aspect, the threshold pressure level is about 30,000 Pa.

In a further aspect of the first operating condition, the valve 52 is in the open position to allow fluid communication from the high pressure reservoir 48 to the buffer reservoir 32. Also in this particular aspect, the flow resistor 58 is selected such that the pressure will rise slowly so that it can be monitored with the pressure sensor 34. The larger the value of the flow resistor 58, the longer the amount of time it will take for the buffer reservoir 32 to reach the threshold pressure level. In a further aspect, the larger the value of the flow resistor 58, the more precisely the threshold pressure level can be set. When the pressure of the buffer reservoir 32 reaches the threshold pressure level, the closed position of the valve 52 is enabled.

In one aspect, the second operating condition comprises the buffer reservoir 32 being in fluid communication with the low pressure reservoir 60, such that a pressure ramp is initiated (during which the electrophoretic separation takes place). In this particular aspect, the pressure ramp is initiated wherein the pressure is varied from a starting pressure value of about 60,000 Pa to an ending pressure value of about −60,000 Pa. In a further aspect, the pressure is varied from a starting pressure value of about 30,000 Pa to an ending pressure value of about −30,000 Pa. In still a further aspect, the pressure is varied from a starting pressure value of about 10,000 Pa to an ending pressure value of about −10,000 Pa. In another aspect, the pressure differential varies with time at a rate from about −1 Pa/s to about −1000 Pa/s. In a further aspect, the pressure differential varies with time at a rate from about −10 Pa/s to about −500 Pa/s. In still a further aspect, the pressure differential varies with time at a rate of about −300 Pa/s.

In this particular aspect, the second operating condition is enabled after a sample to be separated is loaded into the electrophoretic device and the driving voltage is turned on. In this particular aspect, the valve 64 is in the open position to allow fluid communication from the buffer reservoir 32 to the low pressure reservoir 60, enabling a pressure ramp. Also in this particular aspect, the flow resistor 70 is selected to achieve the desired electrophoretic separation performance. More particularly, the lower the value of the flow resistor 70, the faster the pressure ramp is enabled, and the faster the corresponding electrophoretic separation occurs. In contrast, the higher the value of the flow resistor 70, the slower the pressure ramp is enabled, and the slower the corresponding electrophoretic separation occurs.

In one aspect, the third operating condition comprises the high pressure reservoir 48 being in fluid communication with the buffer reservoir 32, such that the buffer reservoir 32 reaches a final pressure level, wherein the variable bulk flow of the fluid is varied. In one particular aspect, the desired final pressure level is a positive value. In a further aspect wherein the electrophoretic device is a GEMBE device 1, the final pressure level is a positive value to avoid flow of the sample matrix into the capillary. In a further aspect, the final pressure level is from about 5,000 Pa to about 60,000 Pa. In still a further aspect, the final pressure level is from about 10,000 Pa to about 50,000 Pa. In yet still a further aspect, the final pressure level is about 30,000 Pa.

In a further aspect of the third operating condition, the valve 52 is in the open position to allow fluid communication from the high pressure reservoir 48 to the buffer reservoir 32. Also in this particular aspect, the flow resistor 58 is selected such that the pressure will rise slowly so that it can be monitored with the pressure sensor 34. The larger the value of the flow resistor 58, the longer the amount of time it will take for the buffer reservoir 32 to reach the final pressure level. In a further aspect, the larger the value of the flow resistor 58, the more precisely the final pressure level can be set.

When the pressure of the buffer reservoir 32 reaches the final pressure level, the closed position of the valve 52 is enabled. Moreover, when the pressure of the buffer reservoir 32 reaches the final pressure level, the driving voltage of the electrophoretic device is turned off. In a further aspect, the valve 38 is opened to vent the buffer reservoir 32 to the ambient atmosphere. In one particular aspect, the valve 38 and the flow resistor 44 are used to vent the buffer reservoir 32 to ambient pressure. In another aspect, the valve 38 and the flow resistor 44 are used to rapidly reduce the applied pressure from the threshold pressure level to the starting pressure value at the beginning of the electrophoretic separation to reduce the required separation time.

Figure 14:
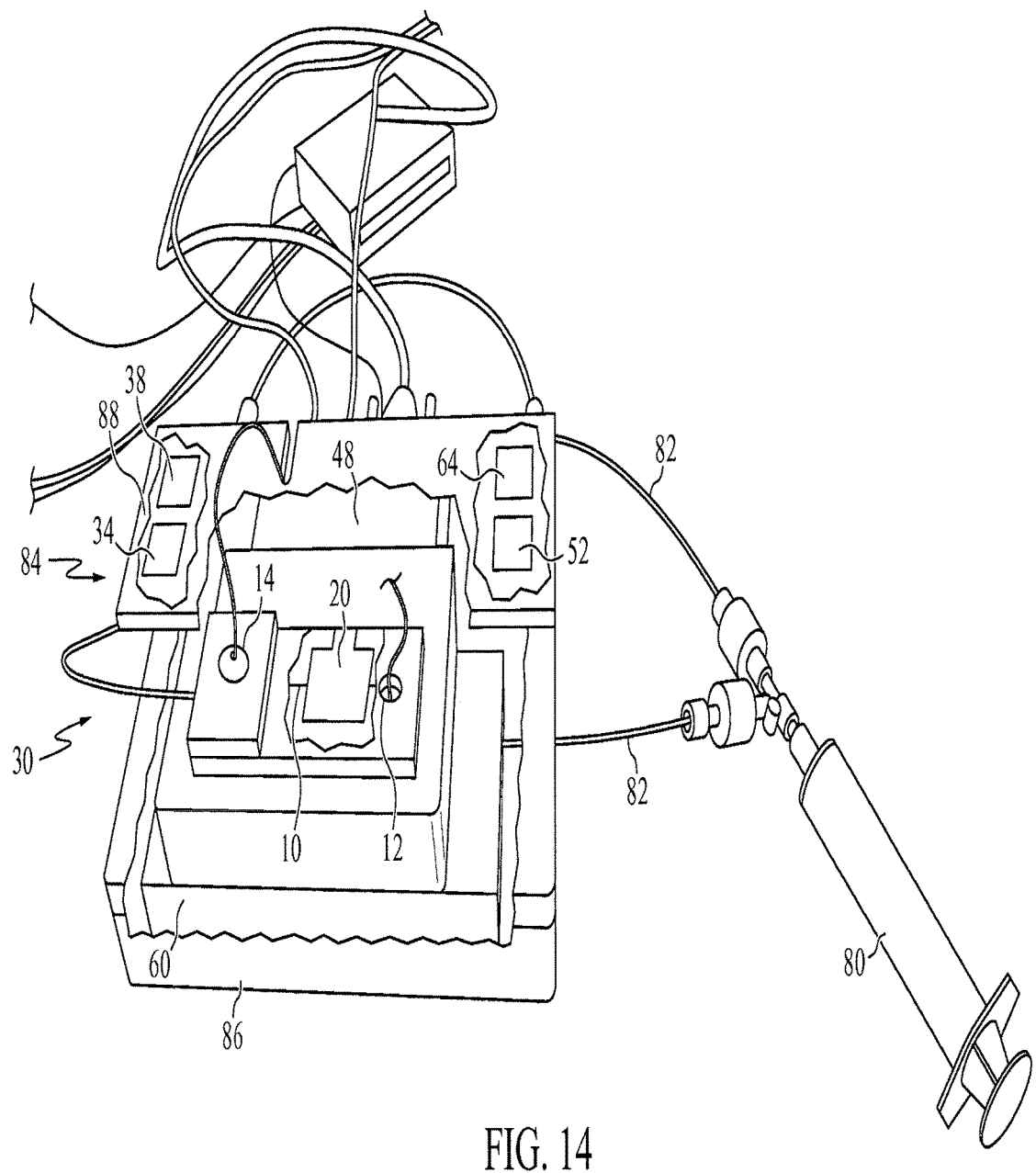
FIG. 14 depicts a GEMBE device for varying with respect to time the bulk flow of a fluid in a separation channel of an electrophoretic device according to an embodiment of the present invention.

As shown in FIG. 14, in still a further aspect, the device 30 for varying with respect to time the bulk flow of a fluid comprises a rigid outer casing 84. In one aspect, the rigid outer casing 84 comprises plastics, polymers, rubbers, metals, composites and/or alloys, and combinations thereof. In one particular aspect, the rigid outer casing 84 comprises a clear acrylic. In a further aspect, the rigid outer casing 84 comprises a bottom 86 and a top 88. In one particular aspect, the bottom 86 is substantially rectangular and the top 88 is substantially rectangular. The shape of the bottom 86 and the top 88 should not be limited to substantially rectangular, however, but may comprise any shape wherein the device 30 for varying with respect to time the bulk flow of a fluid may be accommodated by the rigid outer casing 84.

In a further aspect, the bottom 86 is approximately twice as thick as the top 88. In a further aspect, the bottom 86 is ~25 mm thick and the top 88 is ~12 mm thick. In one particular aspect, the bottom 86 is attached to the top 88 with suitable attachment devices. The attachment devices include but should not be limited to screws, nuts, bolts, clamps, and/or welds. In one particular aspect, the bottom 86 is attached to the top 88 with screws.

In still a further aspect, the rigid outer casing 84 defines spaces for accommodating the buffer reservoir 32, the high pressure reservoir 48, the low pressure reservoir 60, the pressure sensor 34, the valves, 38, 52, 64, and the flow resistors 44, 58, 70. In a further aspect, the top 88 defines spaces for accommodating the buffer reservoir 32, the high pressure reservoir 48, the low pressure reservoir 60, the pressure sensor 34, the valves, 38, 52, 64, and the flow resistors 44, 58, 70. In one particular aspect, the spaces for accommodating the high pressure reservoir 48 and the low pressure reservoir 60 are sealed. In a further aspect, the spaces for accommodating the high pressure reservoir 48 and the low pressure reservoir 60 are sealed with polydimethylsiloxane ("PDMS").

In a further aspect, the device 30 for varying with respect to time the bulk flow of a fluid is portable. Additionally, in one particular aspect, the device 30 for varying with respect to time the bulk flow of a fluid is entirely automated.

In another embodiment, a method of varying with respect to time the bulk flow of a fluid which comprises utilizing the device 30 for varying with respect to time the bulk flow of a fluid in a separation channel 10 of an electrophoretic device 1 having a buffer reservoir 32 in fluid contact with the separation channel 10 according to the present invention is provided.

EXAMPLES

The following non-limiting examples illustrate the methods of the present invention.

Example 1: Acetylcholinesterase Assay with Malaoxon Using Gradient Elution Moving Boundary Electrophoresis Assay Conditions.

A running buffer was prepared consisting of 4-(2-hydroxyethyl)-1-piperazineethanesulfonic acid, i.e. HEPES, at a concentration of ~100 mM and 2-[Bis(2-hydroxyethyl) amino]-2-(hydroxymethyl)-1,3-propanediol, i.e. BIS-TRIS, at a concentration of ~100 mM. The running buffer was prepared at pH ~7.1. EOTrol™ HR (Target Discovery, Palo Alto, Calif.) was added to the run buffer as a dynamic coating to reverse the direction of EOF at a concentration of 1% (by volume).

Prior to reaction, the surface of a polyoxymethylene sample reservoir (Delrin, DuPont, Wilmington, Del.) was passivated with bovine serum albumin (µ2 mg/mL). A sample containing malaoxon (~1 mM) was added to the sample reservoir. Acetylcholine (~500 µM) and acetylcholinesterase (~10.4 nM) were added to the sample reservoir and were allowed to incubate for ~5 min.

A control sample assay was also prepared. In the control sample assay, running buffer was prepared as previously described. the surface of a polyoxymethylene sample reservoir was passivated with bovine serum albumin (2 mg/mL). Acetylcholine (~500 µM) and acetylcholinesterase (~10.4 nM) were added to the sample reservoir and were allowed to incubate for ~5 minutes.

Separation of Acetylcholine and Choline Using Gradient Elution Moving Boundary Electrophoresis.

The reaction mixtures were separately introduced into the inlet end of the separation channel of a GEMBE device, wherein a voltage of ~−2000V was applied on the run buffer reservoir. During the GEMBE separation, the pressure applied to the run buffer reservoir was varied from about 6,000 Pa to about −8,000 Pa at a rate of about −300 Pa/s. The GEMBE device was run for four cycles, wherein the concentration of choline was detected and quantified at four time points. The concentration of choline was detected and quantified after ~2 min, ~5 min, ~7.5 min, and ~10.5 min.

Results.

Figure 2:
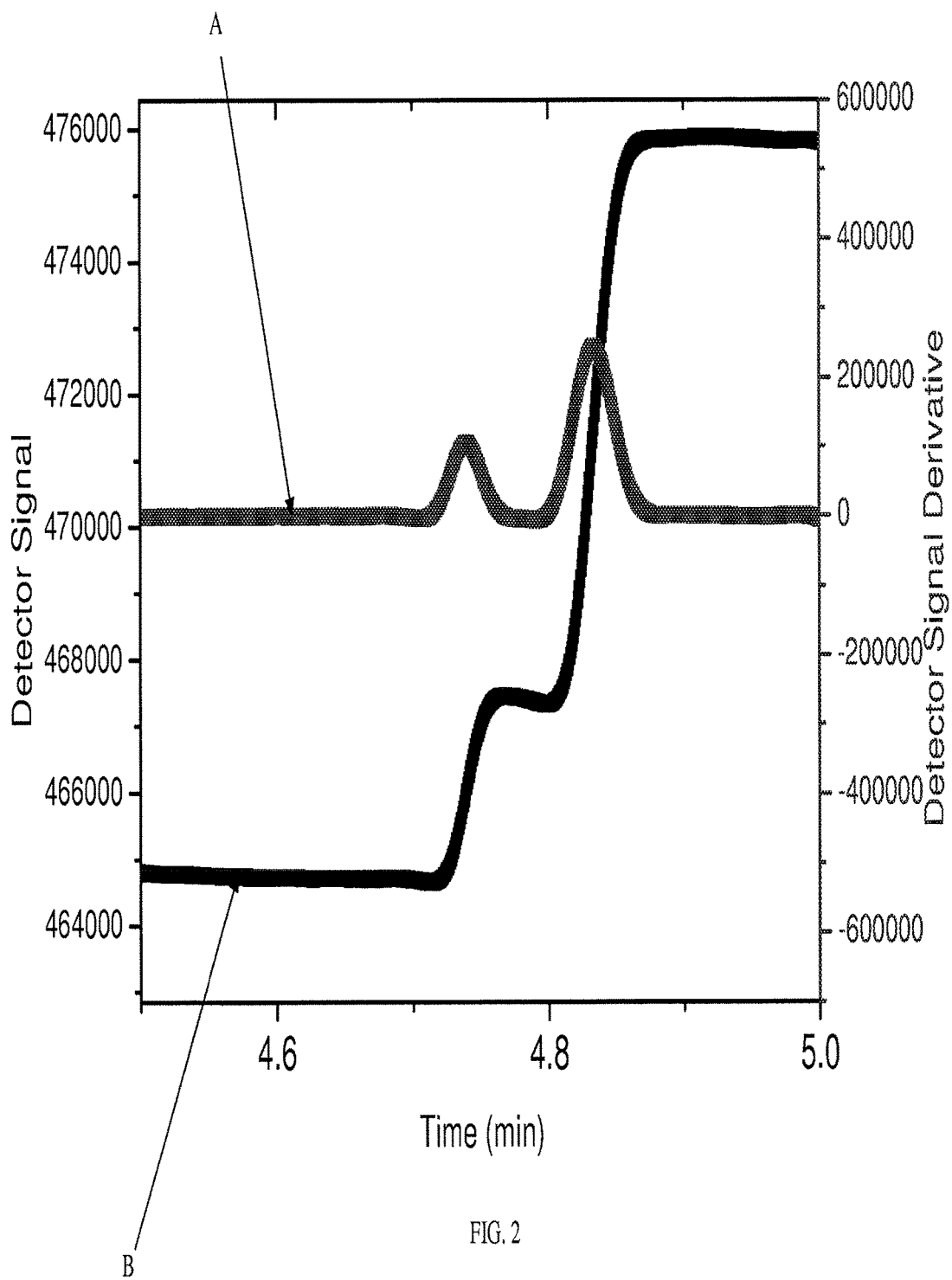
FIG. 2 is a graph of detector response with respect to time for the separation of acetylcholine (~500 µM) and choline in an acetylcholinesterase assay at which the concentration of acetylcholinesterase was ~10.4 nM using a GEMBE device and is a graph of the derivative of the detector response with respect to time for the separation of acetylcholine (~500 µM) and choline in an acetylcholinesterase assay using a GEMBE device.
Figure 3:
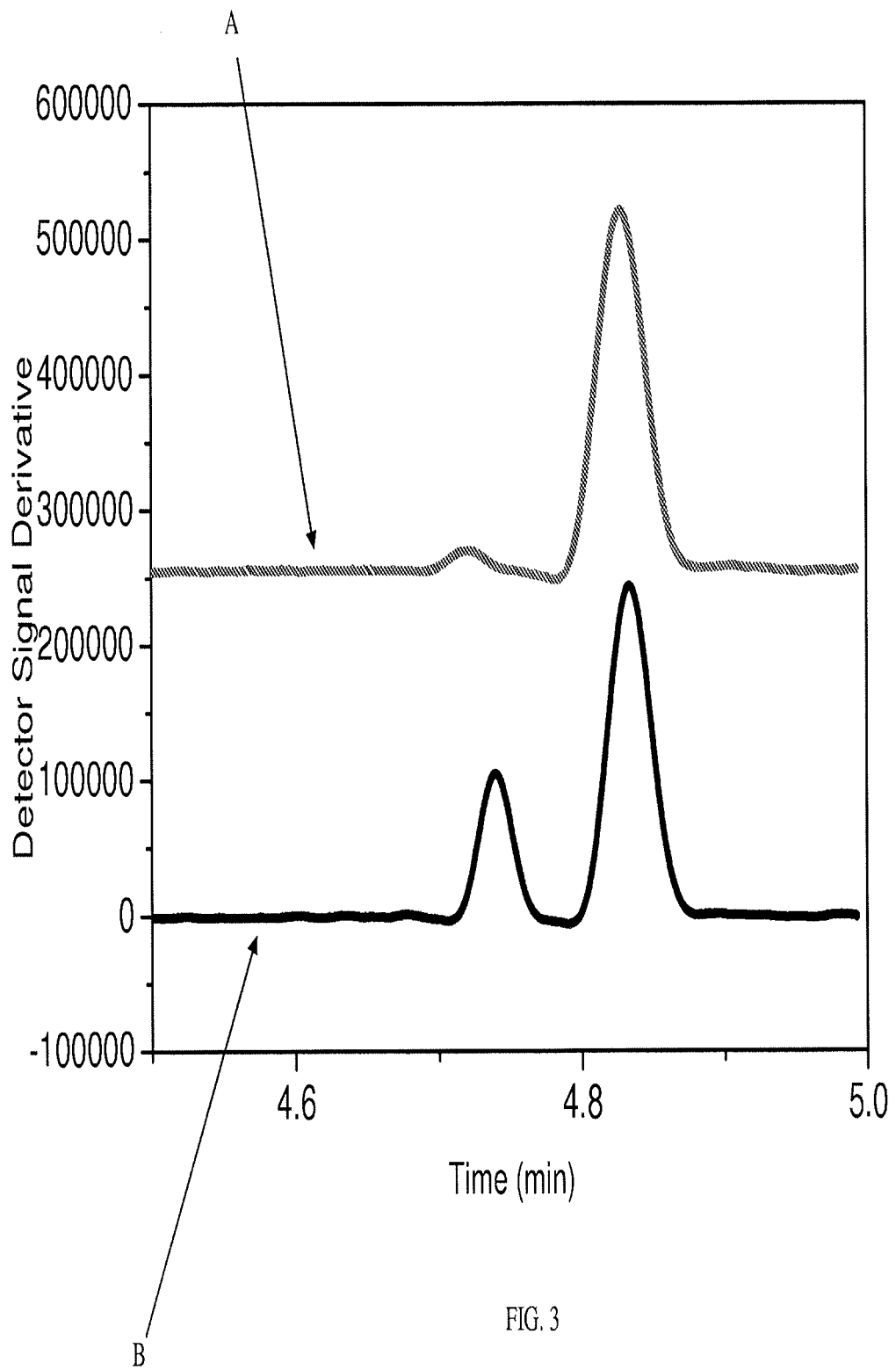
FIG. 3 is a graph of the derivative of the detector response with respect to time for the separation of acetylcholine (~500 µM) and choline in an acetylcholinesterase assay at which the concentration of acetylcholinesterase was ~10.4 nM using a GEMBE device in a control sample and is a graph of the derivative of the detector response with respect to time for the separation of acetylcholine (~500 µM) and choline in an acetylcholinesterase assay using a GEMBE device in the presence of malaoxon (~1 mM)

As indicated by arrow "A", FIG. 2 depicts a graph of detector response with respect to time for the separation of acetylcholine and choline at different rates of bulk flow. As indicated by arrow "B", FIG. 2 also depicts a graph of the derivative of the detector response with respect to time for the separation of acetylcholine and choline in an acetylcholinesterase assay using a GEMBE device and method. As indicated by the arrow "A" shown in FIG. 3, in the presence of malaoxon, an acetylcholinesterase inhibitor, a decrease in the concentration of choline was observed due to the inhibition of acetylcholinesterase by malaoxon. As indicated by the arrow "B" shown in FIG. 3, in the absence of malaoxon, choline is observed, indicating that the acetylcholinesterase degraded the substrate acetylcholine properly.

Figure 4A:
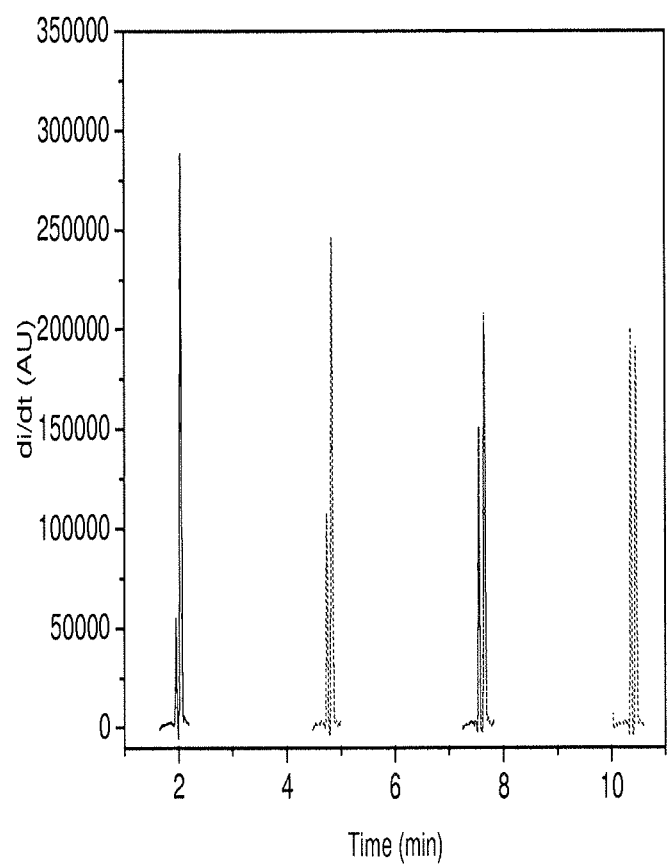
FIG. 4A is a graph of the derivative of the detector response with respect to time for the separation of acetylcholine (~500 µM) and choline in an acetylcholinesterase assay at which the concentration of acetylcholinesterase was ~10.4 nM using a GEMBE device in a control sample, wherein the GEMBE device was run for four cycles.
Figure 4B:
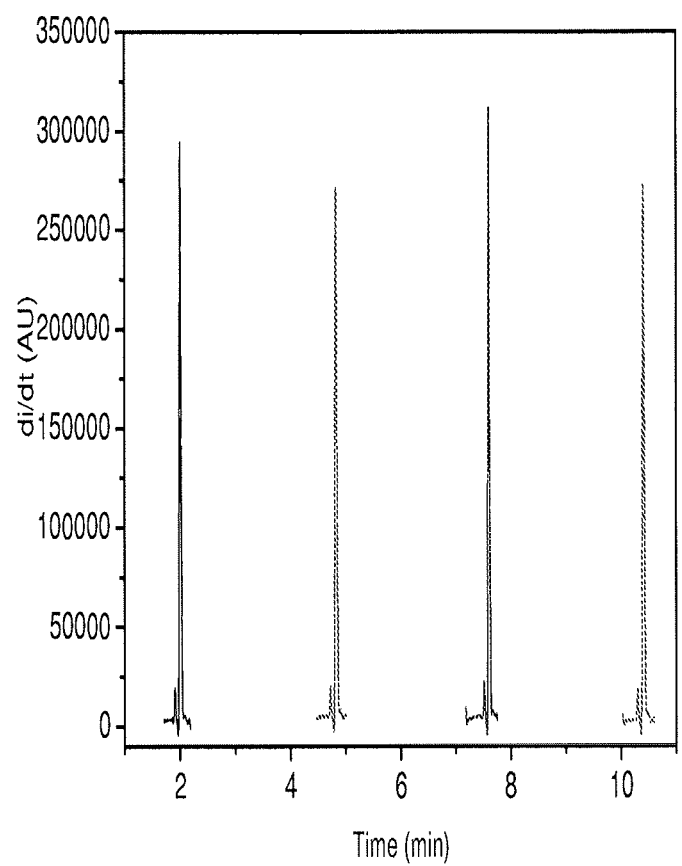
FIG. 4B is a graph of the derivative of the detector response with respect to time for the separation of acetylcholine (~500 µM) and choline in an acetylcholinesterase assay at which the concentration of acetylcholinesterase was ~10.4 nM using a GEMBE device in the presence of malaoxon (~1 mM), wherein the GEMBE device was run for four cycles.

Moreover, as shown in FIGS. 4A and 4B, the activity of acetylcholinesterase was quantified at four time points. More particularly, the activity of acetylcholinesterase was quantified at ~2 min, ~5 min, ~7.5 min, and ~10.5 min.

As shown in FIG. 4A, in the control sample assay, the concentration of choline increases over time. Thus, where no inhibitor of acetylcholinesterase is present, acetylcholinesterase catalyzes the hydrolysis of acetylcholine to acetate and choline. In contrast, as shown in FIG. 4B, in the sample assay wherein ~1 mM of malaoxon was added to the sample reservoir, the concentration of choline does not increase over time. Thus, where an inhibitor of acetylcholinesterase is present, acetycholinesterase no longer catalyzes the hydrolysis of acetylcholine to acetate and choline.

Figure 5:
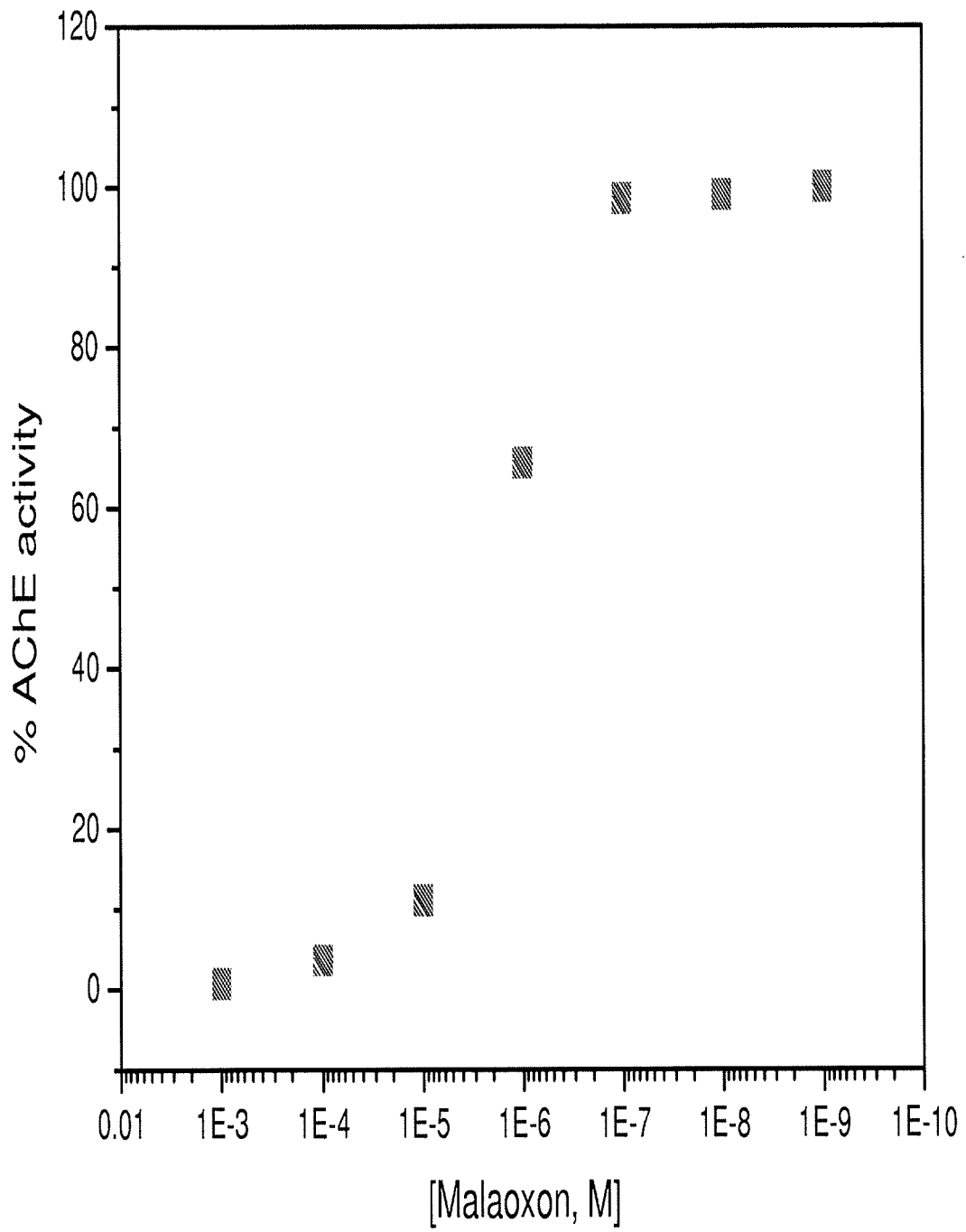
FIG. 5 is a graph of a dose response curve for acetylcholinesterase activity with respect to the concentration of malaoxon.
Figure 6:
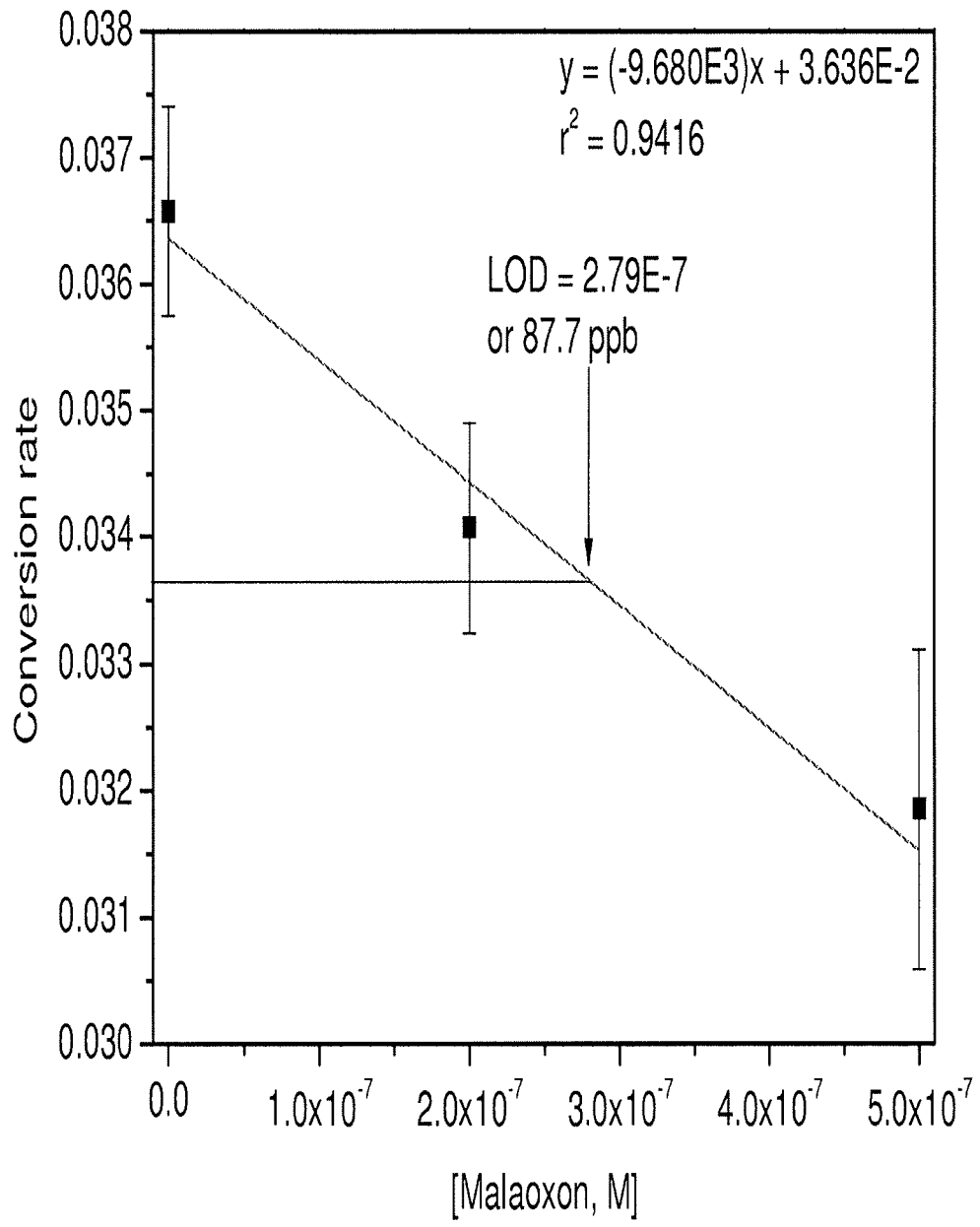
FIG. 6 is a graph of the conversion rate of acetylcholine (~500 µM) to choline in an acetylcholinesterase assay at which the concentration of acetylcholinesterase was ~10.4 nM with respect to the concentration of malaoxon which demonstrates the limit of detection.

Additionally, as shown in FIG. 5, a dose-response curve for malaoxon was procured. Moreover, as shown in FIG. 6, the limit of detection ("LOD") was determined for the detection of malaoxon. As shown in FIG. 6, the LOD was determined to be ~2.79E-7M, or 87.7 parts per billion ("ppb").

Example 2: Acetylcholinesterase Assay with Malaoxon in Complex Samples Using Gradient Elution Moving Boundary Electrophoresis Assay Conditions in Apple Juice.

A running buffer was prepared consisting of 4-(2-hydroxyethyl)-1-piperazineethanesulfonic acid, i.e. HEPES, at a concentration of ~100 mM and 2-[Bis(2-hydroxyethyl)amino]-2-(hydroxymethyl)-1,3-propanediol, i.e. BIS-TRIS, at a concentration of ~100 mM. The running buffer was prepared at pH ~7.1. EOTrol™ HR (Target Discovery, Palo Alto, Calif.) was added to the run buffer as a dynamic coating to reverse the direction of EOF at a concentration of 1% (by volume).

Prior to reaction, the surface of a polyoxymethylene sample reservoir (Delrin, DuPont, Wilmington, Del.) was passivated with bovine serum albumin (~2 mg/mL). A sample containing malaoxon (~1 mM) in filtered apple juice (10× dilution) was added to the sample reservoir. Acetylcholine (~500 μM) and acetylcholinesterase (~10.4 nM) were added to the sample reservoir and were allowed to incubate for ~5 min.

Assay Conditions in Whole Milk.

A running buffer was prepared consisting of 4-(2-hydroxyethyl)-1-piperazineethanesulfonic acid, i.e. HEPES, at a concentration of ~100 mM and 2-[Bis(2-hydroxyethyl)amino]-2-(hydroxymethyl)-1,3-propanediol, i.e. BIS-TRIS, at a concentration of ~100 mM. The running buffer was prepared at pH ~7.1. EOTrol™ HR (Target Discovery, Palo Alto, Calif.) was added to the run buffer as a dynamic coating to reverse the direction of EOF at a concentration of 1% (by volume).

Prior to reaction, the surface of a polyoxymethylene sample reservoir (Delrin, DuPont, Wilmington, Del.) was passivated with bovine serum albumin (2 mg/mL). A sample containing malaoxon (~1 mM) in whole milk (4% milk fat, Giant Food) at a dilution of 10× was added to the sample reservoir. Acetylcholine (~500 μM) and acetylcholinesterase (~10.4 nM) were added to the sample reservoir and were allowed to incubate for ~5 minutes.

Assay Conditions in Soil.

A running buffer was prepared consisting of 4-(2-hydroxyethyl)-1-piperazineethanesulfonic acid, i.e. HEPES, at a concentration of ~100 mM and 2-[Bis(2-hydroxyethyl)amino]-2-(hydroxymethyl)-1,3-propanediol, i.e. BIS-TRIS, at a concentration of ~100 mM. The running buffer was prepared at pH ~7.1. EOTrol™ HR (Target Discovery, Palo Alto, Calif.) was added to the run buffer as a dynamic coating to reverse the direction of EOF at a concentration of 1% (by volume).

Prior to reaction, the surface of a polyoxymethylene sample reservoir (Delrin, DuPont, Wilmington, Del.) was passivated with bovine serum albumin (2 mg/mL). A sample containing malaoxon (~1 mM) in soil was added as a slurry to the sample reservoir. Acetylcholine (~500 μM) and acetylcholinesterase (~10.4 nM) were added to the sample reservoir and were allowed to incubate for ~5 min.

Separation of Acetylcholine and Choline Using Gradient Elution Moving Boundary Electrophoresis.

The reaction mixtures were separately introduced into the inlet end of the separation channel of a GEMBE device, wherein a voltage of ~–2000V was applied on the waste chamber. During the GEMBE separation, the pressure applied to the run buffer reservoir was varied from about 6,000 Pa to about –8,000 Pa at a rate of –300 Pa/s. The concentration of choline was detected and quantified.

Results for Assay in Apple Juice.

Figure 7:
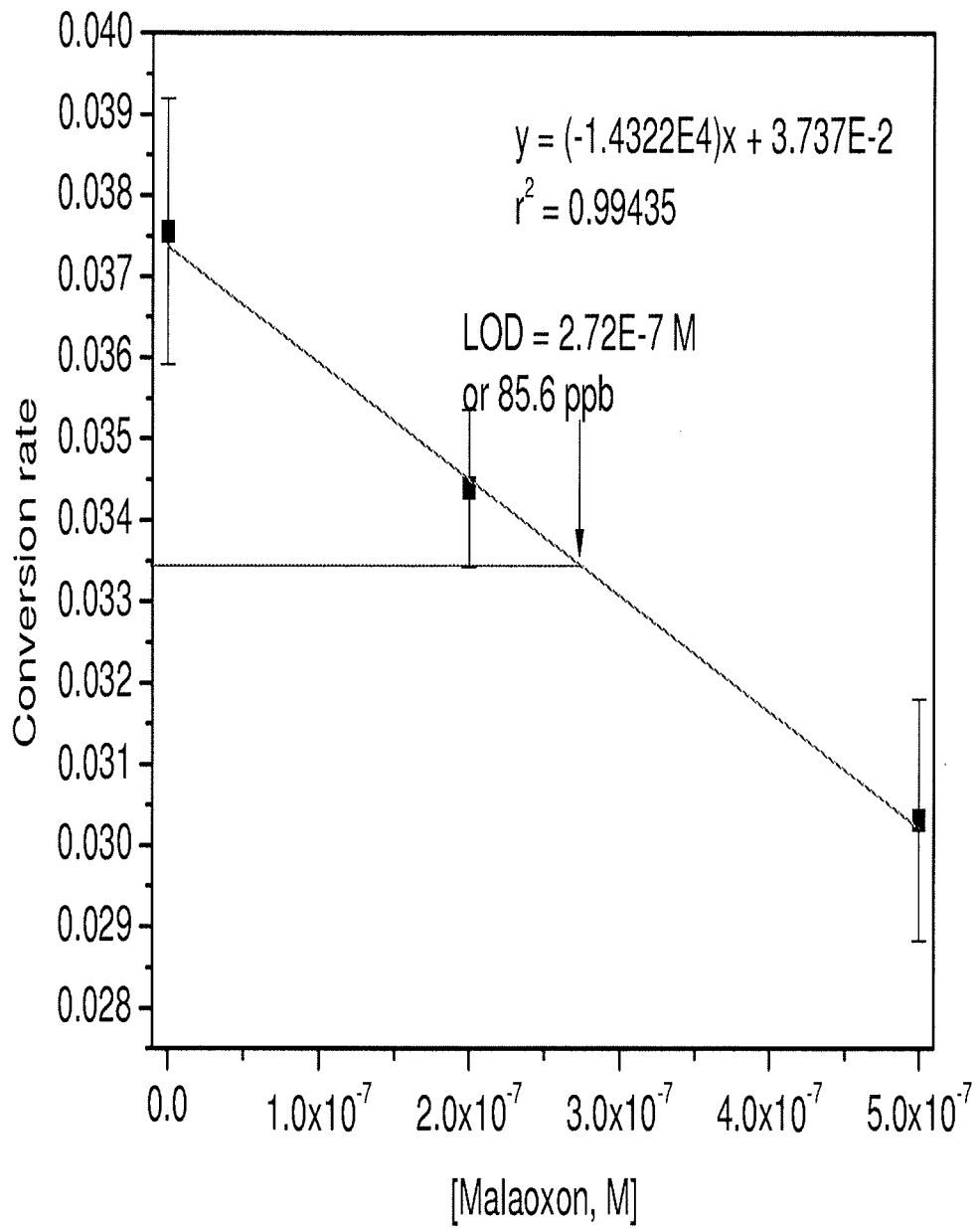
FIG. 7 is a graph of the conversion rate of acetylcholine (~500 µM) to choline in an acetylcholinesterase assay at which the concentration of acetylcholinesterase was ~10.4 nM in apple juice (10× dilution) with respect to the concentration of malaoxon which demonstrates the limit of detection.

As shown in FIG. 7, the LOD of malaoxon in filtered apple juice (10× dilution) was determined. The LOD was determined to be ~2.72E-7M, or 85.6 ppb.

Results for Assay in Whole Milk.

Figure 8:
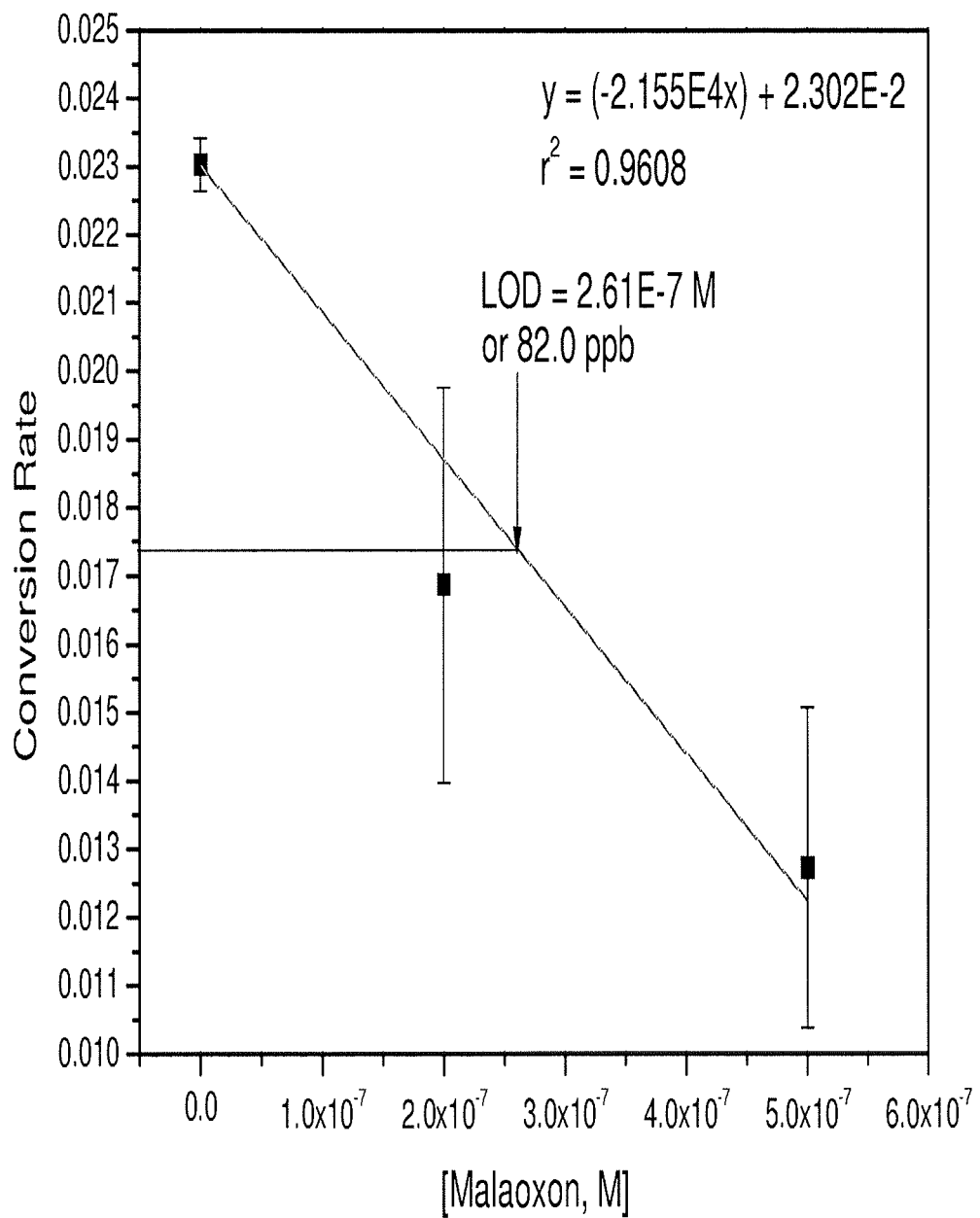
FIG. 8 is a graph of the conversion rate of acetylcholine (~500 µM) to choline in an acetylcholinesterase assay at which the concentration of acetylcholinesterase was ~10.4 nM in whole milk (10× dilution) with respect to the concentration of malaoxon which demonstrates the limit of detection.

As shown in FIG. 8, the LOD of malaoxon in whole milk (10× dilution) was determined. The LOD was determined to be ~2.61E-7M, or 82.0 ppb.

Results for Assay in Soil.

Figure 9:
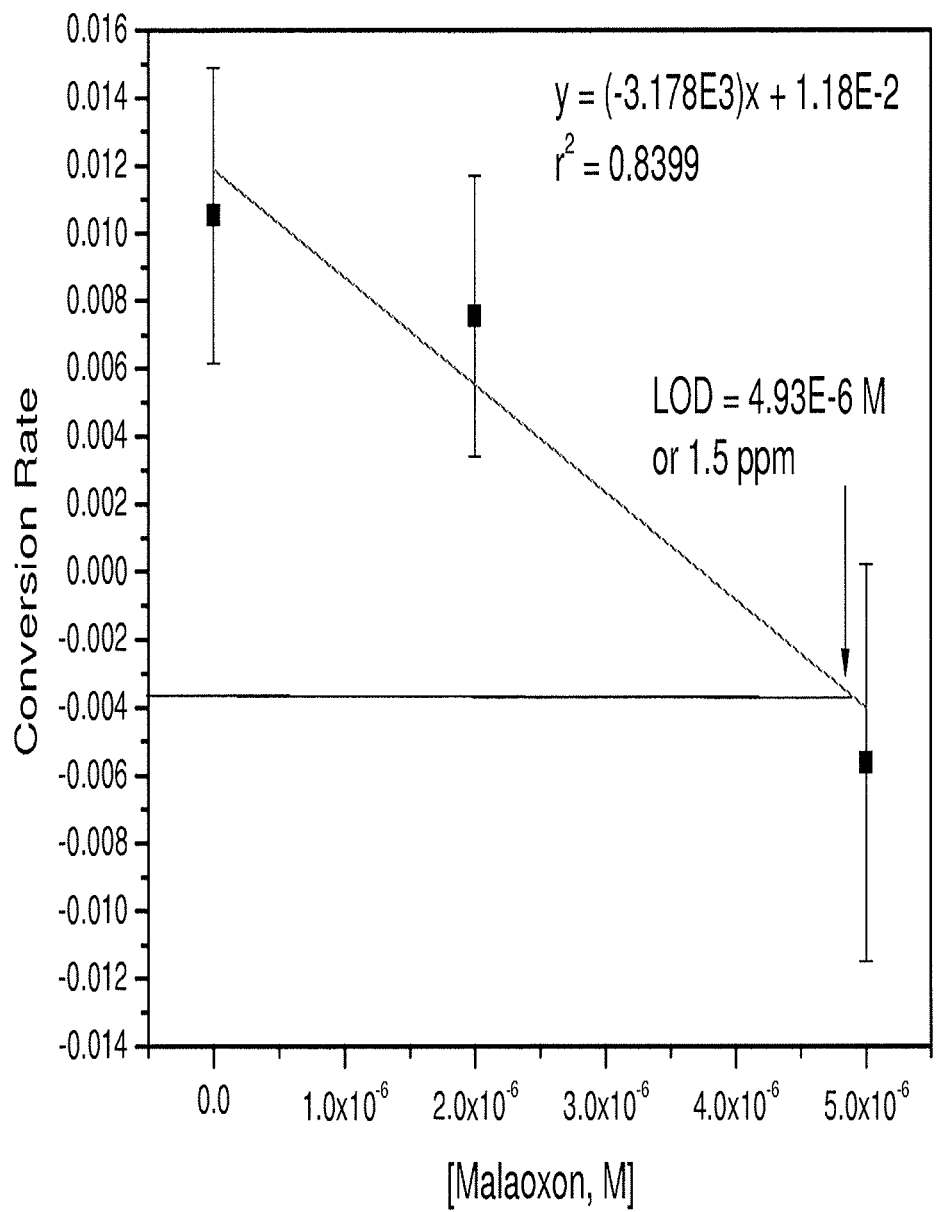
FIG. 9 is a graph of the conversion rate of acetylcholine (~500 µM) to choline in an acetylcholinesterase assay at which the concentration of acetylcholinesterase was ~10.4 nM in soil (added as a slurry to the reaction medium) with respect to the concentration of malaoxon which demonstrates the limit of detection.

As shown in FIG. 9, the LOD of malaoxon in soil (added as a slurry to the sample reservoir) was determined. The LOD was determined to be ~4.93E-6M, or 1.5 parts per million ("ppm").

Example 3: Acetylcholinesterase Assay with Tacrine Using Gradient Elution Moving Boundary Electrophoresis Assay Conditions.

A running buffer was prepared consisting of 4-(2-hydroxyethyl)-1-piperazineethanesulfonic acid, i.e. HEPES, at a concentration of ~100 mM and 2-[Bis(2-hydroxyethyl)amino]-2-(hydroxymethyl)-1,3-propanediol, i.e. BIS-TRIS, at a concentration of ~100 mM. The running buffer was prepared at pH ~7.1. EOTrol™ HR (Target Discovery, Palo Alto, Calif.) was added to the run buffer as a dynamic coating to reverse the direction of EOF at a concentration of 1% (by volume).

Prior to reaction, the surface of a polyoxymethylene sample reservoir (Delrin, DuPont, Wilmington, Del.) was passivated with bovine serum albumin (~2 mg/mL). A sample containing tacrine (~1 μM) was added to the sample reservoir. Acetylcholine (~500 μM) and acetylcholinesterase (~10.4 nM) were added to the sample reservoir and were allowed to incubate for ~5 minutes.

A control sample assay was also prepared. In the control sample assay, running buffer was prepared as previously described. the surface of a polyoxymethylene sample reservoir was passivated with bovine serum albumin (~2 mg/mL). A sample containing tacrine (~1 μM) was added to the sample reservoir. Acetylcholine (~500 μM) and acetylcholinesterase (~10.4 nM) were added to the sample reservoir and were allowed to incubate for ~5 minutes.

Separation of Acetylcholine and Choline Using Gradient Elution Moving Boundary Electrophoresis.

The reaction mixtures were separately introduced into the inlet end of the separation channel of a GEMBE device, wherein a voltage of ~–2000V was applied on the waste chamber. During the GEMBE separation, the pressure applied to the run buffer reservoir was varied from about 6,000 Pa to about –8,000 Pa at a rate of about –300 Pa/s. The concentration of choline was detected and quantified.

Results.

Figure 10:
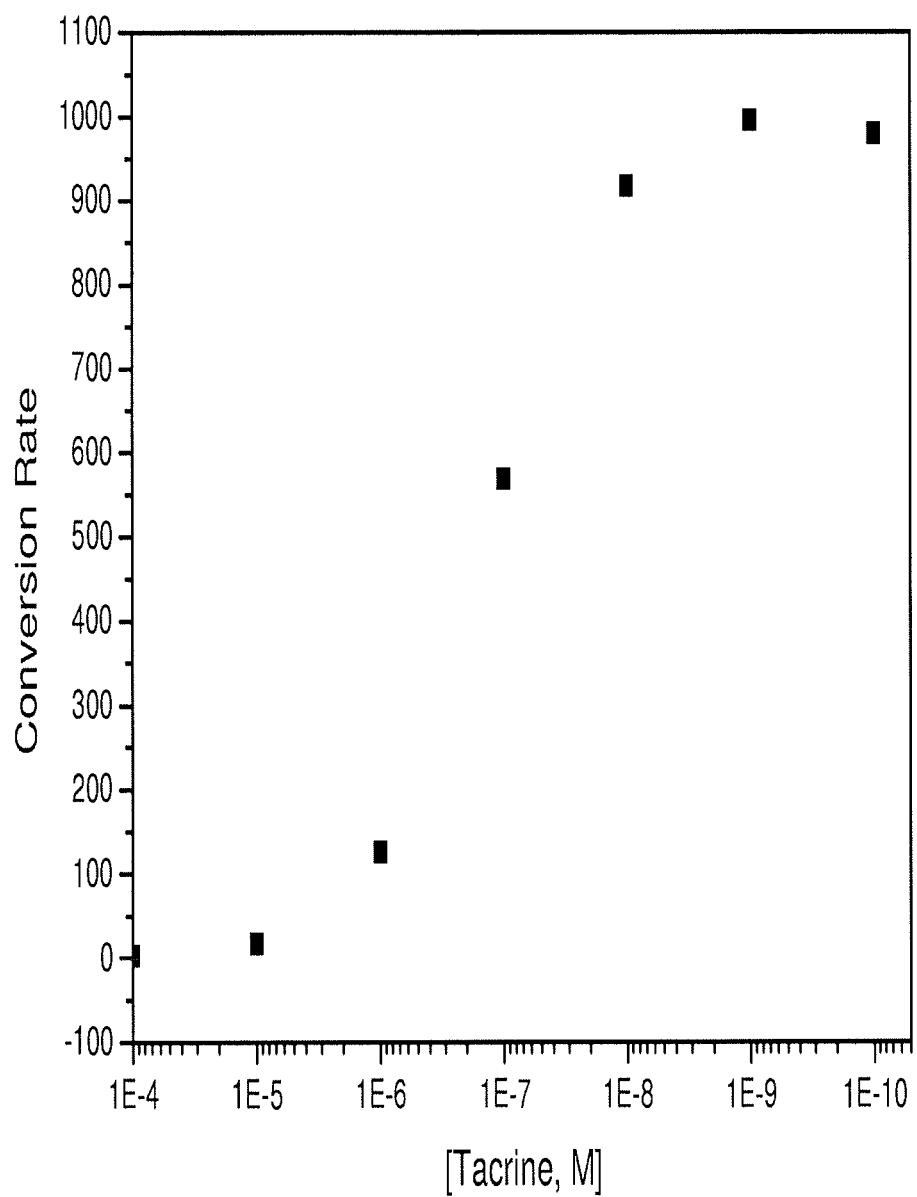
FIG. 10 is a graph of a dose response curve for acetylcholinesterase activity with respect to the concentration of tacrine.
Figure 11:
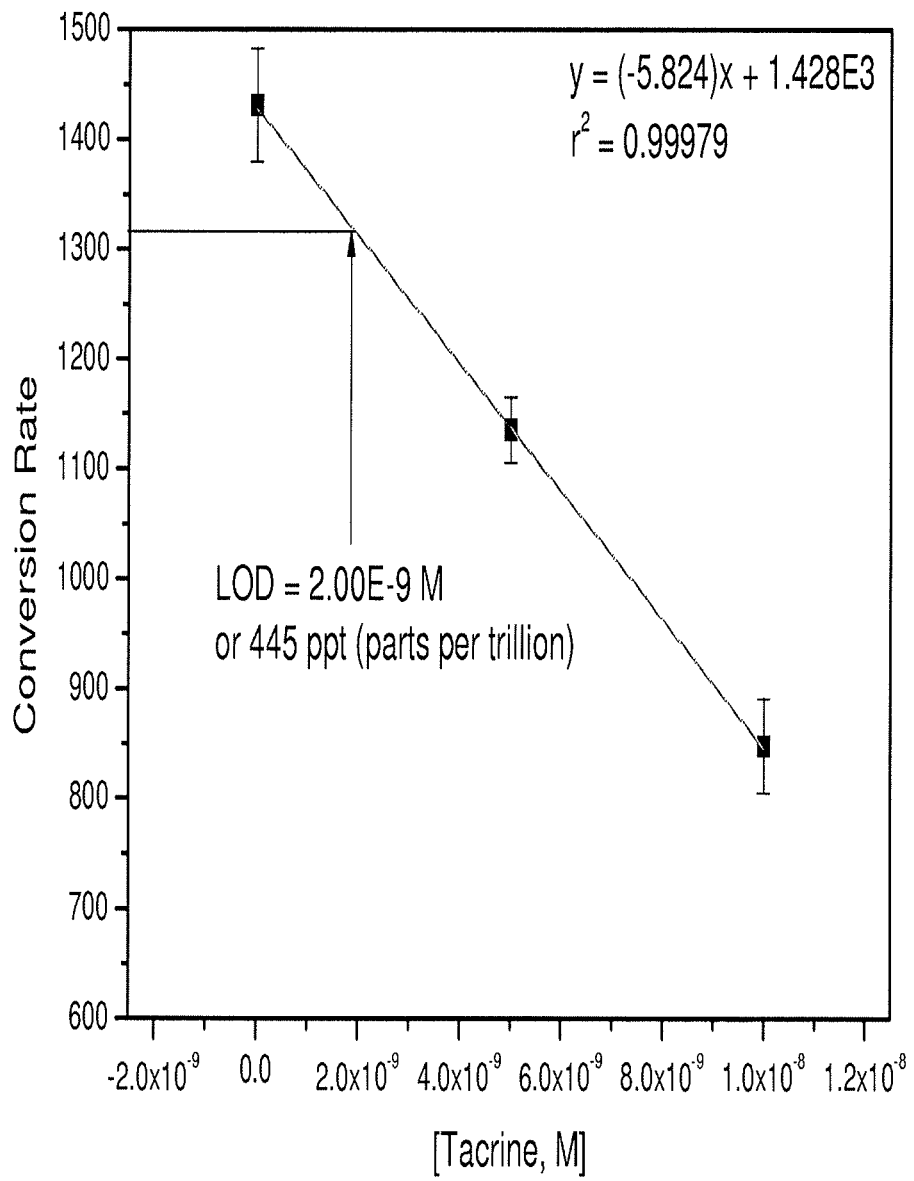
FIG. 11 is a graph of the conversion rate of acetylcholine (~500 µM) to choline in an acetylcholinesterase assay at which the concentration of acetylcholinesterase was ~10.4 nM with respect to the concentration of tracrine which demonstrates the limit of detection.

Additionally, as shown in FIG. 10, a dose-response curve for tacrine was procured. Moreover, as shown in FIG. 11, the LOD was determined in the presence of tacrine. As shown in FIG. 11, the LOD was determined to be ~2.00E-9M, or 445 parts per trillion ("ppt").

Example 4: Separation of Complex Samples Using Gradient Elution Moving Boundary Electrophoresis Materials.

A sample buffer was prepared consisting of 12 mmol/kg L-histidine (Fluka, Milwaukee, Wis.), and 50 mmol/kg acetic acid (Sigma, St. Louis, Mo.) in 18 MΩ cm water with a measured pH ~4.4. Run buffer was prepared identical to the sample buffer but with the addition of approximately 58 µmol/kg didodecyldimethyl-ammonium bromide (Aldrich, St. Louis, Mo.) as a dynamic coating to reverse the direction of the EOF.

Stock solutions of potassium chloride (Mallinckrodt, Hazelwood, Mo.), calcium chloride (Fisher Scientific, Kansas City, Mo.), sodium chloride (Mallinckrodt, Hazelwood, Mo.), magnesium chloride (Fluka, Milwaukee, Wis.), and lithium chloride (Mallinckrodt, Hazelwood, Mo.) were prepared at 1 mol/L in 18 MΩ cm water prior to further dilution using sample buffer. These stock solutions were added to the sample buffer, milk, and dirt (discussed below). A stock solution of melamine (Aldrich, St. Louis, Mo.) was prepared directly in the sample buffer at 10 mmol/L and diluted further with sample buffer.

Whole milk (4% milk fat, Giant Food) was diluted 1000× in sample buffer. Upon addition of the acidic buffer, the milk proteins and fat coagulated into irregular particles.

Dirt was collected from under several oak trees on the Gaithersburg campus of the National Institute of Standards and Technology (Gaithersburg, Md.). The dirt sample was suspended in a sample buffer at a concentration of 5 mg/mL. Each dirt solution was mixed using a vortex mixer for ~5 seconds and placed upright in a holder.

Estuarine sediment (Standard Reference Material 1646a) was suspended in sample buffer at a concentration of 0.28 mg/mL. Coal fly ash (Standard Reference Material 1633b) was prepared in sample buffer at concentrations of 18.8 mg/mL to measure potassium and 0.095 mg/mL to measure calcium, sodium, and magnesium.

Tomato leaves, peach leaves, and citrus leaves were analyzed to show that GEMBE is capable of analyzing cations in a complex matrix of biological material. Tomato leaves (Standard Reference Material 1573a), peach leaves (Standard Reference Material 1547), and citrus leaves (Standard Reference Material 1572) were obtained from the National Institute of Standards and Technology along with their certificates of analysis. The leaves were suspended in sample buffer by mixing with a vortex mixer at 0.060 mg/mL (tomato), 0.070 mg/mL (peach). and 0.065 mg/mL (citrus).

Gradient Elution Moving Boundary Electrophoresis Device.

Reservoirs for the sample buffer and the run buffer were machined from polyoxymethylene and polysulfone, respectively. A 5.5 cm long fused silica capillary (Polymicro Technologies, Phoenix, Ariz.) with an outer diameter of ~363.5 µm and an inner diameter of ~13.5 µm was inserted through holes drilled into the sides of the reservoirs such that the capillary protruded ~1 mm into the sample reservoir and ~5 mm into the run buffer reservoir. Double-sided adhesive tape was affixed between the run buffer reservoir and the high pressure fitting (Upchurch, Vernon Hills, Ill.) to hold the capillary securely in place.

For analyte detection, the capillary was threaded through a TraceDec® contactless conductivity detector. The detection point was ~15 mm from the capillary inlet end into the sample reservoir. Detector settings were the following: frequency, 2× high; voltage, 0 dB; gain, 200%; offset, 14; filter, slow; and data acquisition rate, 19.8 Hz. Constant DC voltage (PS350, Stanford Research Systems) was applied during experiments via high purity platinum wires inserted into the reservoirs. A precision pressure controller (Series 600, Mensor, San Marcos, Tex.), backed by pressurized helium, controlled the pressure inside the sealed run buffer reservoir. Data were recorded using vendor supplied detector software (TraceDec® Monitor 0.07a). Custom LabView software controlled and monitored the pressure controller and high voltage source. The loosely sealed sample reservoir was at ambient pressure. The apparatus was contained inside an enclosure to minimize the effects of temperature fluctuations due to stray air currents on the detector signal.

Separation of Complex Samples.

A new capillary was filled by driving run buffer from the run buffer reservoir through the capillary using pressure. As soon as a bead of fluid was visible on the opposite end of the capillary inserted into the sample reservoir, the sample reservoir was filled with sample buffer. Before initial use, run buffer was flushed through the capillary for several minutes to form a coating of DDAB on the capillary surface. Prior to analysis of a new type of sample, the sample reservoir was rinsed three times with 18 MΩ cm water, rinsed once with the new sample solution, and filled with 200 µL of fresh sample solution for analysis. The sample was replaced between replicate separations. Analyte step/peaks were identified by performing separations of samples comprised of individual analytes prepared in sample buffer. Analysis of blank sample buffer after each sample indicated that contamination of the system by samples was below the limit of detection (LOD) of the apparatus. The apparatus was stored by replacing the fluid in the sample reservoir with 18 MΩ cm water and reducing the pressure to between 2 and 5 kPa.

Separation was effected by holding the pressure on the run buffer reservoir at a high constant pressure between 25 and 60 kPa for ~6 s. The high voltage was switched on, while the pressure was reduced to the starting pressure for that separation, and held for ~10 s. The pressure was subsequently decreased by 100 Pa/s until enough time had elapsed to allow the analytes of interest to elute through the capillary. The capillary was then flushed at high pressure, typically ~5 kPa larger than the pressure applied at the start of the separation, for at least ~10 s. The high voltage was switched off, and the system was held in this configuration for at least ~1 min before the start of the next separation.

DDAB served to reverse EOF in the capillary, so that the EOF opposed the electrophoretic motion of the cations analyzed. In this experiment, DDAB was reported to be unstable over a period of days, as evidenced by a slow shift of analyte elution to higher pressure as EOF in the capillary tended to zero. Rinsing the capillary with 0.1 mol/L sodium hydroxide and recoating with DDAB was therefore necessary once over the course of these experiments.

Data Analysis.

A summary of results obtained for cationic analytes measured in complex samples using GEMBE with contactless conductivity detection is set forth in Table I below.

|  | K | Ca | Na | Mg | Li |
|---|---|---|---|---|---|
| Sample Buffer | | | | | |
| LOD (μmol/L) | 0.22 | 0.31 | 0.67 | 0.27 | 0.39 |
| RSD[a] (%) | 0.45 | 0.49 | 2.40 | 0.71 | 0.44 |
| Milk (Diluted 1000x) | | | | | |
| C (μmol/L) | 44.7 ± 0.9 | 32.1 ± 0.9 | 21.1 ± 0.4 | 5.9 ± 0.4 | |
| recovery[b] (%) | 99 ± 2 | 109 ± 3 | 106 ± 2 | 91 ± 2 | |
| RSD[a] (%) | 0.85 | 0.64 | 0.86 | 1.39 | |
| Dirt (5.0 mg/mL) | | | | | |
| C (μmol/L) | 13.8 ± 0.7 | 142 ± 65 (81.1 ± 2.7)[d] | 7.1 ± 0.8 | 18.8 ± 1.5 | |
| recovery[b] (%) | 100 ± 4.3 | 58 ± 27 | 93 ± 6 | 84 ± 6 | |
| RSD[a] (%) | 0.90 | 1.61 | 3.32 | 1.55 | |
| Estuarine Sediment (0.28 mg/mL) | | | | | |
| C (μmol/L) | 3.6 ± 0.3 | 20.6 ± 1.3 | 54.4 ± 0.9 | 10.3 ± 1.0 | |
| recovery[b] (%) | 5.8 ± 0.8 | 56.8 ± 7.1 | 60.3 ± 6.3 | 23.0 ± 3.3 | |
| RSD[a] (%) | 8.07 | 5.65 | 1.43 | 8.71 | |
| Coal Fly Ash (18.8 mg/mL for K, 0.095 mg/mL for Ca, Na, Mg) | | | | | |
| C (μmol/L) | 26.4 ± 0.5 | 49.4 ± 0.7 | 9.8 ± 1.1 | 12.3 ± 0.9 | |
| recovery[b] (%) | 0.28 ± 0.01 | 138.1 ± 6.5 | 118.0 ± 13.6 | 65.3 ± 5.1 | |
| RSD[a] (%) | 1.88 | 0.16 | 9.99 | 5.51 | |
| Tomato Leaves (0.060 mg/mL) | | | | | |
| C (μmol/L) | 41.4 ± 0.2 | 60.3 ± 1.0 | 1.0 ± 0.6 | 22.7 ± 0.7 | |
| recovery[b] (%) | 99.9 ± 10.2 | 79.8 ± 8.2 | 282 ± 172 | 76.6 ± 8.6 | |
| RSD[a] (%) | 0.08 | 1.13 | 39.3 | 1.25 | |
| Peach Leaves (0.070 mg/mL) | | | | | |
| C (μmol/L) | 40.2 ± 0.5 | 7.9 ± 2.2 | [e] | 13.5 ± 0.7 | |
| recovery[b] (%) | 92.4 ± 9.4 | 29.0 ± 8.6 | | 108.5 ± 12.4 | |
| RSD[a] (%) | 1.31 | 22.6 | | 1.79 | |
| Citrus Leaves (0.065 mg/mL) | | | | | |
| C (μmol/L) | 28.9 ± 0.3 | 13.2 ± 0.5 | [e] | 14.3 ± 0.7 | |
| recovery[b] (%) | 95.5 ± 10.1 | 25.9 ± 2.9 | | 92.2 ± 11.3 | |
| RSV[a] (%) | 0.75 | 1.44 | | 0.72 | |

[a]Relative standard deviation.
[b]Apparent recovery[17] calculated as the ratio of the slope measured for the standard addition curve to the slope measured for the calibration curve with sample buffer.
[c]Apparent recovery[17] calculated as the ratio of the concentration measured using GEMBE to the expected concentration calculated from the SRM certificate and assuming complete dissolution of the analytes.
[d]Value calculated using the calibration curve obtained with sample buffer.
[e]Value below the LOD.

Figure 15A:
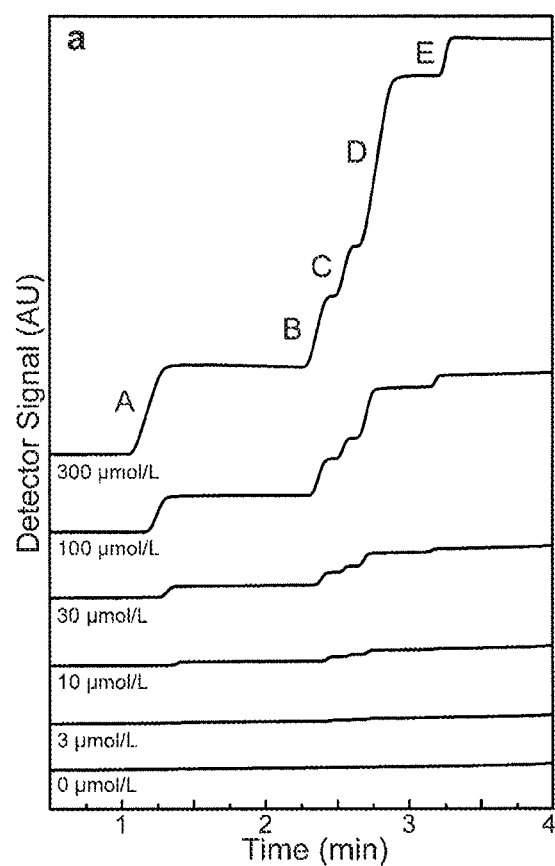
FIG. 15A is a graph of detector response with respect to time for the separation of potassium chloride, calcium chloride, sodium chloride, magnesium chloride, and lithium chloride for 0 µmol/L, 3 µmol/L, 10 µmol/L, 30 µmol/L, 100 µmol/L, and 300 µmol/L using a GEMBE device.
Figure 15B:
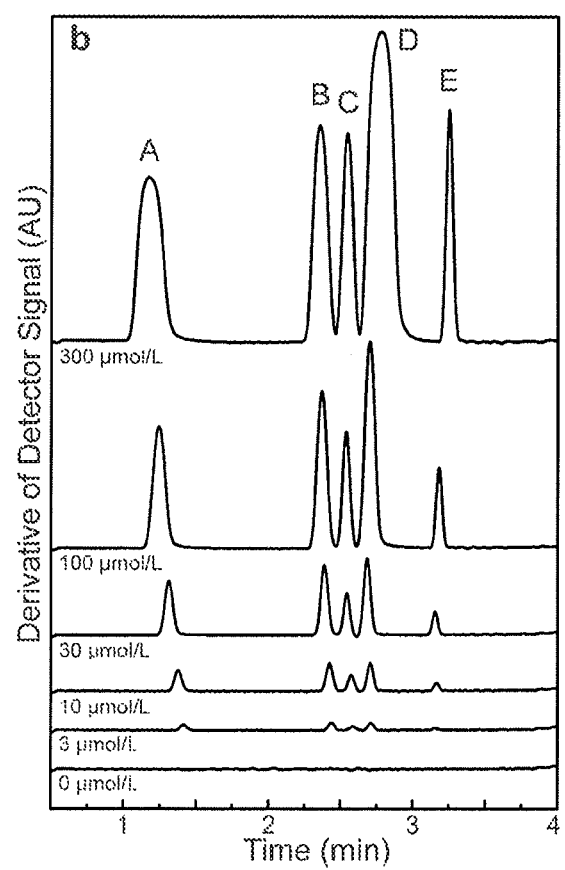
FIG. 15B is a graph of the derivative of the detector response with respect to time for the separation of potassium chloride, calcium chloride, sodium chloride, magnesium chloride, and lithium chloride for 0 µmol/L, 3 µmol/L, 10 µmol/L, 30 µmol/L, 100 µmol/L, and 300 µmol/L using a GEMBE device.

Sample buffer alone with known concentrations of analytes (excluding melamine) was used to characterize the experimental apparatus, optimize the separation parameters, and construct calibration curves. As shown in FIG. 15A, measurements were taken of sample buffer with various concentrations (3, 10, 30, 100, and 300 μmol/L) of each of the inorganic cations potassium, as indicated by "A", calcium, as indicated by "B", sodium, as indicated by "C", magnesium, as indicated by "D", and lithium, as indicated by "E". As shown in FIG. 15B, the data of FIG. 15A was converted to peaks by taking the derivative of the detector signal with respect to time. Quantitative data analysis was performed using Mathematica (Wolfram Research, Champaign, Ill.). Data was binned into ~0.2 s increments for derivation and semi-automated peak finding. The original data, unbinned and undifferentiated was then fit to an error function and a linear offset to account for background signal over a span of time containing the step width on either side of the step. Potassium, lithium, and melamine steps were fit individually, while calcium, sodium, and magnesium steps were fit simultaneously to the sum of these error functions and a linear offset.

Whole Milk Results.

Figure 16:
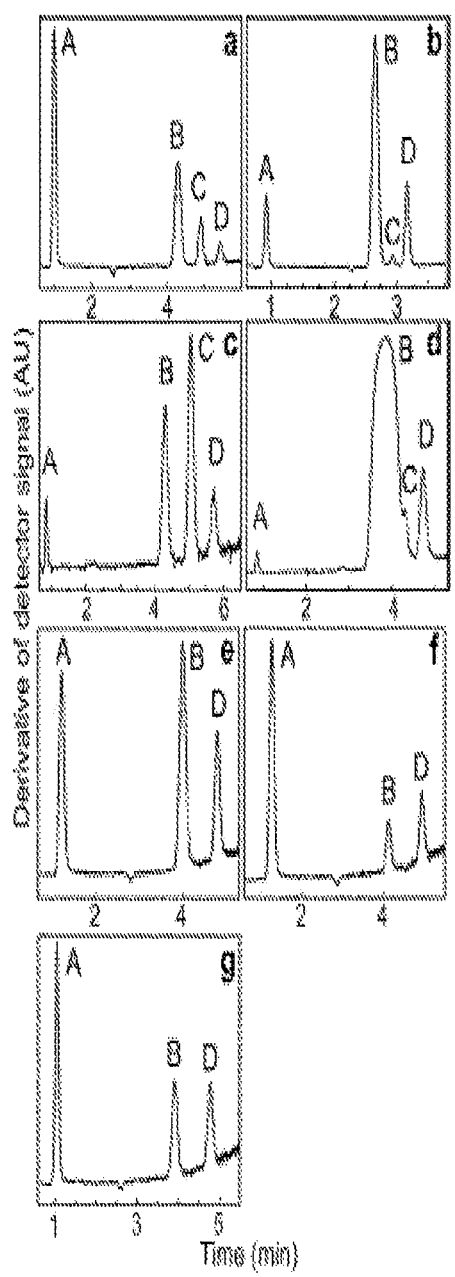
FIG. 16 is a graph of the derivative of the detector response with respect to time for the analysis of milk, dirt, estuarine sediment, coal fly ash, tomato leaf, peach leaf, and citrus leaf with potassium "A", calcium "B", sodium "C", and magnesium "D", using a GEMBE device at an applied voltage of 400 V/cm and applied pressure starting between 47 and 57 kPa and decreasing 100 Pa/s.

No effort was made to avoid pipetting the irregular particles present in the whole milk. A standard addition method was used to assess any matrix effects and provide quantitative measurement of the cation content of the milk. As shown in FIG. 16, depicted in graphs "a", measurements were taken at 10, 20, and 30 μmol/L of each analyte (except lithium and melamine) added to the sample solution. The results are summarized in Table I. Apparent recoveries were calculated as the ratio of the slope measured for the standard addition curve for the milk to the slope measured for the calibration curve with sample buffer. Typical apparent recoveries were within 3 standard deviations of 100% (with the exception of magnesium) indicating minimal interference with diluted milk.

Dirt, Estuarine Sediment, and Coal Fly Ash Results.

As shown in FIG. 16, depicted in graph "b", measurements were taken at 0, 5, 10, and 15 μmol/L of each analyte (except lithium and melamine) added to the dirt solution. The results are summarized in Table I. Potassium, calcium, sodium, and magnesium were present in the dirt at measurable concentrations. Apparent recoveries were calculated as the ratio of the slope measured for the standard addition curve for dirt to the slope measured for the calibration curve with sample buffer. Standard errors for the measured concentrations and recoveries were greater than those for milk, likely due to the greater heterogeneity of the dirt samples.

As shown in FIG. 16, depicted in graph "c", measurements were taken at 0, 5, 10, and 15 μmol/L of each analyte (except lithium and melamine) added to the estuarine sediment solution. Additionally, as shown in FIG. 16, depicted in graph "d", measurements were taken at 0, 5, 10, and 15 μmol/L of each analyte (except lithium and melamine) added to the coal fly ash solution. The results are summarized in Table I. The concentrations were determined using the mean step heights and the calibration curve measured for the sample buffer. Comparison between the measured values and the SRM certificates shows that GEMBE detected approximately ½ of the potassium and the calcium, approximately ⅔ of the sodium, and approximately ¼ of the magnesium that constitute the estuarine sediment and approximately all of the calcium and sodium and approximately ⅔ of the magnesium content of the coal fly ash. These results suggest that much of the potassium, calcium, sodium, and magnesium in the estuarine sediment and coal fly ash remained undissolved or otherwise unavailable for detection using GEMBE.

Leaves Results.

The tomato, peach, and citrus leaves suspended in sample buffer were analyzed in triplicate for the presence of potassium, calcium, sodium, and magnesium. As shown in FIG. 16, depicted in graph "e", measurements were taken at 0, 5, 10, and 15 μmol/L of each analyte (e.g. potassium, calcium, sodium, and magnesium) added to the tomato leaves in sample buffer. Additionally, as shown in FIG. 16, depicted in graph "f", measurements were taken at 0, 5, 10, and 15 μmol/L of each analyte (e.g. potassium, calcium, sodium, and magnesium) added to the peach leaves in sample buffer. Also, as shown in FIG. 16, depicted in graph "g", measurements were taken at 0, 5, 10, and 15 μmol/L of each analyte (e.g. potassium, calcium, sodium, and magnesium) added to the citrus leaves in sample buffer. The results are summarized in Table I.

Apparent recoveries were calculated as the ratio of the concentration measured using GEMBE and the expected concentration calculated from the SRM certificate, along with the assumption of complete dissolution of these elements in to the sample buffer. Comparison to the SRM certificates revealed that approximately all of the potassium and magnesium, and approximately ⅓ (peach and citrus) or approximately ⅔ (tomato) of the calcium present in the samples was dissolved and measureable using GEMBE.

It is noted that terms like "preferably," "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of indirectly detecting the presence of toxins in a complex sample using electrophoretic separations, the method comprising:
   introducing a run buffer into a separation channel having an inlet end;
   introducing the complex sample into a sample reservoir in fluid contact with the separation channel, wherein the complex sample was subject to no sample preparation or was subject to sample preparation selected from the group consisting of dilution, suspension, filtration, and combinations thereof;
   reacting the complex sample with a signaling enzyme in a reaction medium containing a substrate for the signaling enzyme, wherein the signaling enzyme converts the substrate to a product;
   separating the substrate and the product by:
      applying an electric potential across the separation channel to achieve electrophoretic migration of the substrate and the product, and
      varying with respect to time the bulk flow of the run buffer through the separation channel to achieve selective introduction of the substrate and the product into the inlet end of the separation channel and differential migration of the substrate and the product therethrough such that the substrate and the product are sequentially detected and quantified; and
   determining a rate of conversion of the substrate to the product, wherein a change in the rate of conversion is indicative of the presence of toxins.

2. The method of claim 1, wherein the rate of conversion is determined by comparing the rate of conversion of the substrate to the product with a control rate of conversion of a control sample assay.

3. The method of claim 1, wherein the substrate and the product are sequentially detected and quantified at a single time point.

4. The method of claim 1, wherein the signaling enzyme is chosen from oxidoreductases, transferases, hydrolases, lyases, isomerases, and ligases.

5. The method of claim 4, wherein the signaling enzyme is chosen from acetylcholinesterase and adenylate cyclase.

6. The method of claim 5, wherein the substrate is chosen from acetylcholine and adenosine triphosphate.

7. The method of claim 5, wherein the product is chosen from choline and cyclic adenosine monophosphate.

8. The method of claim 1, wherein the complex sample comprises at least one toxin chosen from nerve agents, pesticides, and endotoxins.

9. The method of claim 1, wherein the complex sample comprises at least one toxin chosen from tabun, sarin, soman, cyclosarin, tacrine, VE, VG, VM, VR, VX, Novichok agents, dichlorvos, malathion, parathion, and malaoxon.

10. The method of claim 1, wherein the complex sample is chosen from soil, mud, dirt, milk, apple juice, estuarine sediment, coal fly ash, blood serum, tomato leaves, peach leaves, citrus leaves, and calf serum.

11. The method of claim 1, wherein the substrate and the product are separated via gradient elution moving boundary electrophoresis (GEMBE).

12. A method of indirectly detecting the presence of toxins in a complex sample using electrophoretic separations, the method comprising:
   introducing a run buffer into a separation channel having an inlet end;
   preparing the complex sample for the electrophoretic separation, wherein the preparing is selected from the group consisting of diluting the complex sample in sample buffer, suspending the complex sample in sample buffer, and combinations thereof;
   introducing the complex sample into a sample reservoir in fluid contact with the separation channel;
   reacting the complex sample with a signaling enzyme in a reaction medium containing a substrate for the signaling enzyme, wherein the signaling enzyme converts the substrate to a product;
   separating the substrate and the product by:
      applying an electric potential across the separation channel to achieve electrophoretic migration of the substrate and the product, and
      varying with respect to time the bulk flow of the run buffer through the separation channel to achieve selective introduction of the substrate and the product into the inlet end of the separation channel and differential migration of the substrate and the product therethrough such that the substrate and the product are sequentially detected and quantified; and
   determining a rate of conversion of the substrate to the product, wherein a change in the rate of conversion is indicative of the presence of toxins.

* * * * *